(12) United States Patent
Rabiner

(10) Patent No.: US 7,806,900 B2
(45) Date of Patent: Oct. 5, 2010

(54) APPARATUS AND METHODS FOR DELIVERY OF REINFORCING MATERIALS TO BONE

(75) Inventor: Robert A. Rabiner, Tiverton, RI (US)

(73) Assignee: IlluminOss Medical, Inc., East Providence, RI (US)

( * ) Notice: Subject to any disclaimer, the term of this patent is extended or adjusted under 35 U.S.C. 154(b) by 831 days.

(21) Appl. No.: 11/789,907

(22) Filed: Apr. 26, 2007

(65) Prior Publication Data

US 2008/0039854 A1    Feb. 14, 2008

Related U.S. Application Data

(60) Provisional application No. 60/795,626, filed on Apr. 26, 2006, provisional application No. 60/858,202, filed on Nov. 10, 2006, provisional application No. 60/880,646, filed on Jan. 16, 2007.

(51) Int. Cl.
*A61B 17/58* (2006.01)
(52) U.S. Cl. .............................. 606/92; 606/94; 600/178
(58) Field of Classification Search ................... 606/92, 606/93, 94, 62–68; 604/21; 600/101, 116, 600/178; 623/23.62, 23.48, 23.58
See application file for complete search history.

(56) References Cited

U.S. PATENT DOCUMENTS

| 4,280,233 | A | 7/1981 | Raab ............................. 3/1.91 |
| 4,294,251 | A | 10/1981 | Greenwald et al. ........... 128/276 |
| 4,313,434 | A | 2/1982 | Segal ........................... 128/92 |
| 4,341,691 | A | 7/1982 | Anuta ......................... 523/116 |
| 4,462,394 | A | 7/1984 | Jacobs ......................... 182/92 |
| 4,686,973 | A | 8/1987 | Frisch .......................... 128/92 |
| 4,697,584 | A | 10/1987 | Haynes ........................ 128/92 |
| 4,735,625 | A | 4/1988 | Davidson ..................... 623/16 |
| 4,870,953 | A | 10/1989 | DonMicheal et al. ......... 604/22 |
| 4,888,024 | A | 12/1989 | Powlan ........................ 623/23 |
| 4,904,391 | A | 2/1990 | Freeman ..................... 210/695 |
| 4,961,424 | A | 10/1990 | Kubota et al. ............. 128/24 A |

(Continued)

FOREIGN PATENT DOCUMENTS

WO    WO 2004/0112661    12/2004    .................... 17/88

(Continued)

OTHER PUBLICATIONS

International Search Report based on PCT/US08/81929 dated Jan. 12, 2009.

(Continued)

*Primary Examiner*—Pedro Philogene
(74) *Attorney, Agent, or Firm*—Greenberg Traurig, LLP; David J. Dykeman; Danielle T. Abramson

(57) ABSTRACT

An apparatus and methods for delivery of reinforcing materials to a weakened or fractured bone is disclosed. An apparatus for delivering a reinforcing mixture to a bone including a tube having a proximal end, a distal end, and a longitudinal axis therebetween, wherein the tube has at least one inner lumen capable of allowing a bone reinforcing mixture to pass therethrough; a balloon engaging the tube wherein the balloon expands from a substantially deflated state to a substantially inflated state upon the bone reinforcing mixture entering the balloon; and at least one light guide extending through the tube into the balloon to guide a light into the balloon.

40 Claims, 18 Drawing Sheets

U.S. PATENT DOCUMENTS

| | | | |
|---|---|---|---|
| 4,963,151 A | 10/1990 | Ducheyne et al. | 623/16 |
| 4,969,888 A | 11/1990 | Scholten et al. | 606/94 |
| 5,030,093 A | 7/1991 | Mitnick | 433/164 |
| 5,049,157 A | 9/1991 | Mittelmeier et al. | 623/16 |
| 5,092,899 A | 3/1992 | Forte | 623/23 |
| 5,102,413 A | 4/1992 | Poddar | 606/62 |
| 5,108,404 A | 4/1992 | Scholten et al. | 606/94 |
| 5,303,718 A | 4/1994 | Krajicek | 128/897 |
| 5,316,550 A | 5/1994 | Forte | 623/23 |
| 5,336,699 A | 8/1994 | Cooke et al. | 523/115 |
| 5,372,598 A | 12/1994 | Luhr et al. | 606/69 |
| 5,391,144 A | 2/1995 | Sakurai et al. | 604/22 |
| 5,423,850 A | 6/1995 | Berger | 606/192 |
| 5,443,468 A | 8/1995 | Johnson | 606/80 |
| 5,462,552 A | 10/1995 | Kiester | 606/92 |
| 5,480,400 A | 1/1996 | Berger | 606/60 |
| 5,554,111 A | 9/1996 | Morrey et al. | 604/26 |
| 5,556,429 A | 9/1996 | Felt | 623/16 |
| 5,658,310 A | 8/1997 | Berger | 606/192 |
| 5,705,181 A | 1/1998 | Cooper et al. | 424/426 |
| 5,707,374 A | 1/1998 | Schmidt | 606/85 |
| 5,795,353 A | 8/1998 | Felt | 623/18 |
| 5,824,087 A | 10/1998 | Aspden et al. | 623/16 |
| 5,827,289 A | 10/1998 | Reiley et al. | 606/86 |
| 5,888,220 A | 3/1999 | Felt et al. | 623/17 |
| 5,897,557 A | 4/1999 | Chin et al. | 606/71 |
| 5,908,433 A | 6/1999 | Eager et al. | 606/170 |
| 6,019,761 A | 2/2000 | Gustilo | 606/62 |
| 6,019,774 A | 2/2000 | Weiss et al. | 606/167 |
| 6,033,411 A | 3/2000 | Preissman | 606/99 |
| 6,039,762 A | 3/2000 | McKay | 623/17 |
| 6,042,380 A | 3/2000 | De Rowe | 433/173 |
| 6,059,789 A | 5/2000 | Dinger et al. | 606/96 |
| 6,066,154 A | 5/2000 | Reiley et al. | 606/192 |
| 6,079,868 A | 6/2000 | Rydell | 366/189 |
| 6,110,176 A | 8/2000 | Shapira | 606/80 |
| 6,121,341 A | 9/2000 | Sawhney et al. | 522/84 |
| 6,127,597 A | 10/2000 | Beyar et al. | 623/16 |
| 6,140,452 A | 10/2000 | Felt et al. | 528/60 |
| 6,179,852 B1 | 1/2001 | Strickland et al. | 606/167 |
| 6,200,134 B1 | 3/2001 | Kovac et al. | 433/29 |
| 6,217,581 B1 | 4/2001 | Tolson | 606/86 |
| 6,224,630 B1 | 5/2001 | Bao et al. | 623/17 |
| 6,241,734 B1 | 6/2001 | Scribner et al. | 606/93 |
| 6,248,110 B1 | 6/2001 | Reiley et al. | 606/93 |
| 6,248,131 B1 | 6/2001 | Felt et al. | 623/17.12 |
| 6,290,382 B1 | 9/2001 | Bourn et al. | 362/554 |
| 6,299,597 B1 * | 10/2001 | Buscemi et al. | 604/101.03 |
| 6,306,177 B1 | 10/2001 | Felt et al. | 623/23.6 |
| 6,336,914 B1 | 1/2002 | Gillespie, III | 604/165.01 |
| 6,336,930 B1 | 1/2002 | Stalcup et al. | 606/69 |
| 6,358,252 B1 | 3/2002 | Shapira | 606/80 |
| 6,395,007 B1 | 5/2002 | Bhatnagar et al. | 606/94 |
| 6,416,737 B1 | 7/2002 | Manolagas et al. | 424/9.2 |
| 6,423,083 B2 | 7/2002 | Reiley et al. | 606/192 |
| 6,425,923 B1 * | 7/2002 | Stalcup et al. | 623/23.58 |
| 6,440,444 B2 | 8/2002 | Boyce et al. | 424/422 |
| 6,443,988 B2 | 9/2002 | Felt et al. | 623/17.12 |
| 6,458,375 B1 | 10/2002 | Gertzman et al. | 424/423 |
| 6,478,751 B1 | 11/2002 | Krueger et al. | 600/566 |
| 6,485,512 B1 | 11/2002 | Cheng | 623/1.21 |
| 6,494,883 B1 | 12/2002 | Ferree | 606/61 |
| 6,524,251 B2 | 2/2003 | Rabiner et al. | 600/439 |
| 6,551,337 B1 | 4/2003 | Rabiner et al. | 606/169 |
| 6,565,528 B1 * | 5/2003 | Mueller | 604/106 |
| 6,579,277 B1 | 6/2003 | Rabiner et al. | 604/525 |
| 6,579,279 B1 | 6/2003 | Rabiner et al. | 604/528 |
| 6,620,185 B1 | 9/2003 | Harvie et al. | 606/232 |
| 6,648,881 B2 | 11/2003 | KenKnight et al. | 606/32 |
| 6,652,547 B2 | 11/2003 | Rabiner et al. | 606/129 |
| 6,652,587 B2 | 11/2003 | Felt et al. | 623/20.16 |
| 6,660,013 B2 | 12/2003 | Rabiner et al. | 606/122 |
| 6,679,873 B2 | 1/2004 | Rabiner et al. | 604/528 |
| 6,695,781 B2 | 2/2004 | Rabiner et al. | 600/129 |
| 6,695,782 B2 | 2/2004 | Rabiner et al. | 600/439 |
| 6,696,073 B2 | 2/2004 | Boyce et al. | 424/422 |
| 6,719,773 B1 | 4/2004 | Boucher et al. | 606/192 |
| 6,730,048 B1 | 5/2004 | Hare et al. | 601/2 |
| 6,733,451 B2 | 5/2004 | Rabiner et al. | 600/439 |
| 6,740,093 B2 * | 5/2004 | Hochschuler et al. | 606/94 |
| 6,755,862 B2 | 6/2004 | Keynan | 623/16.11 |
| 6,802,835 B2 | 10/2004 | Rabiner et al. | 604/528 |
| 6,818,018 B1 | 11/2004 | Sawhney | 623/11.11 |
| 6,852,095 B1 | 2/2005 | Ray | 604/93.01 |
| 6,866,678 B2 | 3/2005 | Shenderova et al. | 607/88 |
| 6,875,212 B2 | 4/2005 | Shaolian et al. | 606/61 |
| 6,885,246 B2 | 4/2005 | Tsutsui et al. | 330/285 |
| 6,887,246 B2 | 5/2005 | Bhatnagar et al. | 606/94 |
| 6,887,275 B2 | 5/2005 | Carchidi et al. | 623/17.17 |
| 6,899,713 B2 | 5/2005 | Shaolian et al. | 606/61 |
| 6,899,719 B2 | 5/2005 | Reiley et al. | 606/192 |
| 6,964,667 B2 | 11/2005 | Shaolian et al. | 606/99 |
| 6,979,341 B2 | 12/2005 | Scribner et al. | 606/192 |
| 6,981,981 B2 | 1/2006 | Reiley et al. | 606/192 |
| 7,001,431 B2 | 2/2006 | Bao et al. | 623/17.12 |
| 7,008,433 B2 | 3/2006 | Voellmicke et al. | 606/93 |
| 7,052,498 B2 | 5/2006 | Levy et al. | 606/63 |
| 7,077,865 B2 | 7/2006 | Bao et al. | 623/17.12 |
| 7,124,067 B2 | 10/2006 | Ascenzi | 703/11 |
| 7,141,061 B2 | 11/2006 | Williams et al. | 623/1.11 |
| 7,144,414 B2 | 12/2006 | Harvie et al. | 606/232 |
| 7,153,305 B2 | 12/2006 | Johnson et al. | 606/90 |
| 7,156,880 B2 | 1/2007 | Evans et al. | 623/23.51 |
| 7,320,709 B2 | 1/2008 | Felt et al. | 623/20.16 |
| 7,407,616 B2 | 8/2008 | Melikechi et al. | 264/494 |
| 7,427,295 B2 * | 9/2008 | Ellman et al. | 623/17.16 |
| 7,628,800 B2 * | 12/2009 | Sherman et al. | 606/279 |
| 2001/0011174 A1 | 8/2001 | Reiley et al. | 606/86 |
| 2001/0044626 A1 | 11/2001 | Reiley et al. | 606/53 |
| 2002/0156482 A1 | 10/2002 | Scribner et al. | 606/92 |
| 2002/0198526 A1 | 12/2002 | Shaolian et al. | 606/61 |
| 2003/0105469 A1 | 6/2003 | Karmon | 606/92 |
| 2003/0229372 A1 | 12/2003 | Reiley et al. | 606/192 |
| 2004/0006341 A1 | 1/2004 | Shaolian et al. | 606/61 |
| 2004/0034434 A1 | 2/2004 | Evans et al. | 623/23.51 |
| 2004/0059333 A1 | 3/2004 | Carl et al. | 606/61 |
| 2004/0092948 A1 | 5/2004 | Stevens et al. | 606/96 |
| 2004/0117025 A1 | 6/2004 | Reindel | 623/18.11 |
| 2004/0167625 A1 | 8/2004 | Beyar et al. | 623/11.11 |
| 2004/0225296 A1 | 11/2004 | Reiss et al. | 606/90 |
| 2004/0230309 A1 | 11/2004 | Di Mauro et al. | 623/17 |
| 2004/0247641 A1 | 12/2004 | Felt et al. | 424/423 |
| 2005/0010231 A1 | 1/2005 | Myers | 606/86 |
| 2005/0043808 A1 | 2/2005 | Felt | 623/20.14 |
| 2005/0119662 A1 | 6/2005 | Reiley et al. | 606/92 |
| 2005/0142315 A1 | 6/2005 | DeSimone et al. | 428/36.9 |
| 2005/0149022 A1 | 7/2005 | Shaolian et al. | 606/61 |
| 2005/0159749 A1 | 7/2005 | Levy et al. | 606/72 |
| 2005/0234453 A1 | 10/2005 | Shaolian et al. | 606/61 |
| 2005/0251140 A1 | 11/2005 | Shaolian et al. | 606/61 |
| 2005/0284485 A9 | 12/2005 | Nelson et al. | 128/848 |
| 2006/0009550 A1 | 1/2006 | Messersmith et al. | 524/17 |
| 2006/0036253 A1 | 2/2006 | Leroux et al. | 606/73 |
| 2006/0100547 A1 | 5/2006 | Rabiner et al. | 601/2 |
| 2006/0100635 A1 | 5/2006 | Reiley et al. | 606/90 |
| 2006/0100706 A1 | 5/2006 | Shadduck et al. | 623/17.11 |
| 2006/0111726 A1 | 5/2006 | Felt et al. | 606/86 |
| 2006/0155296 A1 | 7/2006 | Richter | 606/94 |
| 2006/0173464 A1 | 8/2006 | Ellman et al. | 606/99 |
| 2006/0183811 A1 | 8/2006 | Melikechi et al. | 522/2 |
| 2006/0184246 A1 | 8/2006 | Zwirkoski | 623/11.11 |
| 2006/0195165 A1 | 8/2006 | Gertner et al. | 607/86 |
| 2006/0217747 A1 | 9/2006 | Ferree | 606/151 |
| 2006/0229617 A1 | 10/2006 | Meller et al. | 606/62 |

| | | | |
|---|---|---|---|
| 2006/0247787 A1 | 11/2006 | Rydell et al. | 623/21.11 |
| 2006/0253102 A1 | 11/2006 | Nance et al. | 604/525 |
| 2006/0264950 A1 | 11/2006 | Nelson et al. | 606/72 |
| 2006/0264951 A1 | 11/2006 | Nelson et al. | 606/72 |
| 2006/0264952 A1 | 11/2006 | Nelson et al. | 606/72 |
| 2006/0265077 A1 | 11/2006 | Zwirkoski | 623/17.16 |
| 2006/0271061 A1 | 11/2006 | Beyar et al. | 606/105 |
| 2006/0276819 A1 | 12/2006 | Osorio et al. | 606/192 |
| 2006/0282169 A1 | 12/2006 | Felt et al. | 623/20.11 |
| 2007/0027547 A1 | 2/2007 | Rydell et al. | 623/21.18 |
| 2007/0067032 A1 | 3/2007 | Felt et al. | 623/14.12 |
| 2007/0118143 A1 | 5/2007 | Ralph et al. | 606/92 |
| 2007/0123877 A1 | 5/2007 | Goldin et al. | 606/62 |
| 2007/0198023 A1 | 8/2007 | Sand et al. | 606/92 |
| 2007/0225705 A1 | 9/2007 | Osario et al. | 606/60 |
| 2007/0255287 A1 | 11/2007 | Rabiner | 606/94 |
| 2008/0039854 A1 | 2/2008 | Rabiner | 606/92 |
| 2008/0103505 A1 | 5/2008 | Fransen | 606/92 |
| 2008/0125784 A1 | 5/2008 | Rabiner et al. | 606/92 |
| 2008/0188858 A1 | 8/2008 | Luzzi et al. | 606/94 |
| 2008/0234820 A1 | 9/2008 | Felt et al. | 623/14.12 |
| 2009/0054900 A1 | 2/2009 | Rabiner et al. | 606/93 |
| 2009/0112196 A1 | 4/2009 | Rabiner et al. | 606/13 |

FOREIGN PATENT DOCUMENTS

| | | | | |
|---|---|---|---|---|
| WO | WO 2005/0112804 | | 12/2005 | 17/72 |

OTHER PUBLICATIONS

International Search Report based on PCT/US08/81924 dated Feb. 9, 2009.

International Search Report based on PCT/US08/87630 dated Feb. 24, 2009.

PCT International Search Report based on PCT/US07/10050 dated Apr. 17, 2008.

PCT International Search Report based on PCT/US07/20402 dated Apr. 1, 2008.

PCT International Search Report based on PCT/US07/10038 dated Aug. 27, 2008.

Office Action in U.S. Appl. No. 11/789,906 mailed Apr. 29, 2009.

Jovanovic et al., *Fixion Nails for Humeral Fractures*, Injury, Int. J. Care Injured, vol. 34, Issue 11, pp. 1140-1142, Nov. 2004.

Maruyama et al.,*Metacarpal Fracture Fixation with Absorbable Polyglycolide Rods and Stainless SteleK Wires; A Biomechanical Comparison*, Journal of Biomedical Materials Research (Applied Biomaterials), vol. 33, pp. 9-12, 1996.

Waris et al.,*Bioabsorbable Miniplating Versus Metallic Fixation for Metacarpal Fracturgs*,Clinical Orthopaedics and Related Research, No. 410, pp. 310-319, May 2003.

Waris et al., *Self-Reinforced Bioabsorbable Versus Metallic Fixation Systems for Metacarpal and Phalangeal Fractures: A Biomechanical Study*, The Journal of Hand Surgery, vol. 27A, No. 27A, No. 5, pp. 902-909, Sep. 2002.

Office Action in U.S. Appl. No. 11/789,906 mailed Mar. 11, 2010.

Office Action in U.S. Appl. No. 11/789,906 mailed Apr. 30, 2010.

Office Action in U.S. Appl. No. 11/903,123 mailed Jul. 1, 2010.

\* cited by examiner

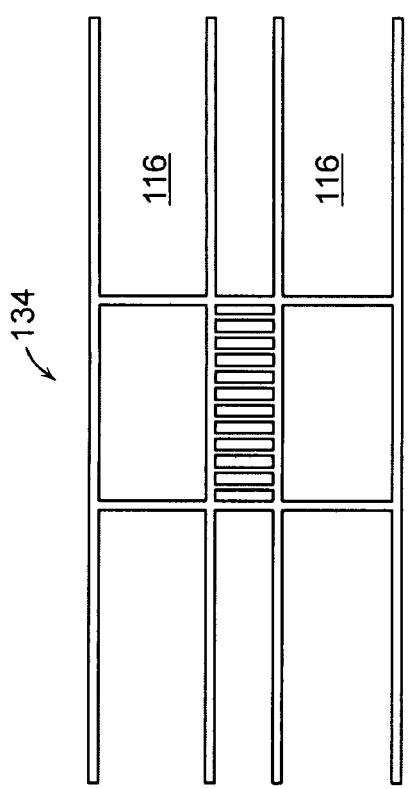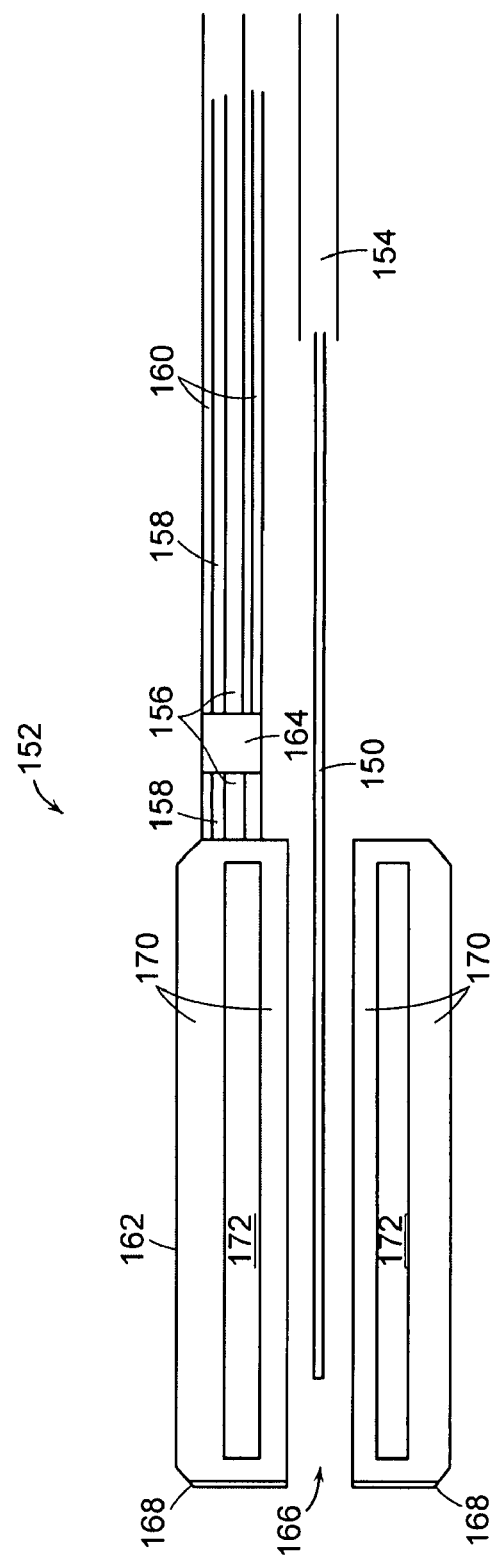

US 7,806,900 B2

APPARATUS AND METHODS FOR DELIVERY OF REINFORCING MATERIALS TO BONE

RELATED APPLICATIONS

This application claims the benefit of U.S. Provisional Application Ser. No. 60/795,626, filed on Apr. 26, 2006, U.S. Provisional Application Ser. No. 60/858,202, filed Nov. 10, 2006, and U.S. Provisional Application Ser. No. 60/880,646, filed Jan. 16, 2007, and the entirety of all these applications are hereby incorporated herein by reference for the teachings therein.

FIELD

The embodiments disclosed herein relate to bone strengthening and reinforcing, and more particularly to apparatus and methods for delivery of reinforcing materials to a weakened or fractured bone.

BACKGROUND

Bone is a living tissue and plays a structural role in the body. Bone consists of repeating Harvesian systems (concentric layers of lamellae deposited around a central canal containing blood vessels and nerves). The central canal is also known as the medullary cavity and is filled with bone marrow. Within the shaft of a long bone, many of these Harvesian systems are bundled together in parallel, forming a kind of bone called compact bone, which is optimized to handle compressive and bending forces. In some bones, such as the metacarpals, the bones themselves are hollow and contain little, if any, marrow. Near the ends of the bones, where the stresses become more complex, the Harvesian systems splay out and branch to form a meshwork of cancellous or spongy bone. Compact bone and cancellous bone differ in density, or how tightly the tissue is packed together.

Collagen rods support the bone and are surrounded by minerals (including calcium and phosphorus) from the blood that crystallize and surround the collagen rods. These minerals give the bones strength while the collagen rods provide resiliency.

Genetic or developmental irregularities, trauma, chronic stress, tumors, and disease can result in pathologies of bones. Some bone diseases that weaken the bones include, but are not limited to, osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, and scoliosis. Weakened bones are more susceptible to fracture, and treatment to prevent bone fractures becomes important. Severe fractures, such as those that are open, multiple, or to the hip or back, are treated in a hospital. Surgery may be necessary when a fracture is open, severe, or has resulted in severe injury to the surrounding tissues. Severe fractures may require internal devices, such as screws, rods, or plates to hold the bone in place or replace lost bone during the healing process.

In many cases where the bone has fractured, a bone cement mixture, or a bone void filler, is added into the bone to repair and strengthen the bone. Prior art bone cement mixtures are typically two part (powder and liquid), require a catalyst, and are exothermic. Injection devices are used to inject bone cement into bone. A typical bone cement injection device has a pistol-shaped body, which supports a cartridge containing bone cement where the injection device is usually a high pressure delivery source. More specifically, a trigger actuates a spring-loaded or screw ram, which forces a volume of bone cement in a viscous condition through a suitable nozzle and into the interior of a bone targeted for treatment. The amount of bone cement mixture injected is a function of the amount of space within the bone structure and the ability to reach the open areas in the bone. In some cases, the presence of bone marrow restricts the amount of bone cement mixture that can be used.

In thermal characterization tests of polymethylmethacrylate (PMMA) bone cement performed according to the ASTM Standard Specification for Acrylic Bone Cement, time and temperature profiles of bone cement were observed to be sensitive to the thickness of the cement patty and the mold material. Due to the heat transfer from the cement to the surrounding mold, such tests might underestimate the exothermic temperature of bone cement. That is, the mold material and geometry may influence the values of the parameters measured.

Bone cements may be difficult to work with and cause complications. Leakage of bone cements can result in soft tissue damage as well as nerve root pain and compression. Other complications associated with the use of bone cements for vertebroplasty and kyphoplasty procedures may include pulmonary embolism, respiratory and cardiac failure, abdominal intrusions, ileus, and death.

Prior art techniques for adding a bone cement mixture to repair or strengthen bone are described in U.S. Pat. No. 4,969,888 entitled "Surgical Protocol for Fixation of Osteoporotic Bone Using Inflatable Device," U.S. Pat. No. 5,108,404 entitled "Surgical Protocol for Fixation of Osteoporotic Bone Using Inflatable Device," U.S. Pat. No. 5,824,087 entitled "Bone Regeneration," U.S. Pat. No. 6,241,734 entitled "Systems and Methods for Placing Materials Into Bone," U.S. Pat. No. 6,395,007 entitled "Apparatus and Method for Fixation of Osteoporotic Bone," U.S. Pat. No. 6,425,923 entitled "Contourable Polymer Filled Implant," U.S. Pat. No. 6,887,246 entitled "Apparatus and Method for Fixation of Osteoporotic Bone," U.S. Pat. No. 6,875,212 entitled "Cureable media for implantable medical device," U.S. Pat. No. 6,964,667 entitled "Formed in place fixation system with thermal acceleration," U.S. Publication No. 2004/0225296 entitled "Devices and methods using an expandable body with internal restraint for compressing cancellous bone," and U.S. Publication No. 2005/0142315 entitled "Liquid perfluoropolymers and medical applications incorporating same."

The prior art injection devices are typically invasive and have difficulty quickly terminating the flow of cement should the cavity fill before the spring-actuated load cycle is completed. Conventional cement injection devices also have difficulty adjusting or controlling the injection volume or injection rate in real time in reaction to cancellous bone volume and density conditions encountered inside the bone.

Thus, there is a need in the art for apparatuses and methods for delivering reinforcing materials into a bone using minimally invasive techniques, with ease of use, greater rate and volume control, and a faster response time.

SUMMARY

Systems and methods for reinforcing weakened or fractured bone are disclosed herein. According to aspects illustrated herein, there is provided an apparatus for delivering a reinforcing mixture to a bone including a tube having a proximal end, a distal end, and a longitudinal axis therebetween, wherein the tube has at least one inner lumen capable of allowing a bone reinforcing mixture to pass therethrough; a balloon engaging the tube wherein the balloon expands from a substantially deflated state to a substantially inflated state upon the bone reinforcing mixture entering the balloon; and at least one light guide extending through the tube into the balloon to guide a light into the balloon.

According to aspects illustrated herein, there is provided an apparatus for delivering a reinforcing mixture to a bone including a catheter having a proximal end, a distal end, and a longitudinal axis therebetween, wherein the catheter has at least one inner lumen capable of allowing a bone reinforcing mixture to pass therethrough; a balloon extending from the catheter wherein the balloon begins to expand from a substantially deflated state to a substantially inflated state as the bone reinforcing mixture enters the balloon; and a junction connecting the catheter to the balloon, wherein the junction concentrates stress applied to the catheter at the junction.

According to aspects illustrated herein, there is provided a method for reinforcing a bone including penetrating the bone to gain access to a cavity in the bone; inserting a balloon catheter into the cavity in the bone; infusing a bone reinforcing mixture into a balloon of the balloon catheter through at least one lumen of a catheter; and activating a light source to harden the bone reinforcing mixture in the balloon.

According to aspects illustrated herein, there is provided a method for reinforcing a bone including penetrating the bone to gain access to a cavity in the bone; inserting a balloon into the cavity in the bone; infusing a bone reinforcing mixture into the balloon through at least one lumen of a catheter connected to the balloon; and separating the catheter from the balloon at a predetermined site.

Various embodiments provide certain advantages. Not all embodiments of the invention share the same advantages and those that do may not share them under all circumstances. Further features and advantages of the embodiments, as well as the structure of various embodiments are described in detail below with reference to the accompanying drawings.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 10 shows a cross-sectional view of an illustrative embodiment of a switch for an illumination band area of a catheter;

FIG. 11 shows a cross-sectional view of an illustrative embodiment of a balloon catheter;

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Apparatuses and methods for the controlled delivery of reinforcing materials to weakened or fractured bones are disclosed herein. An apparatus and methods for the inflation of a balloon within the lumen of a bone to reduce a fracture is disclosed herein. Apparatus and methods disclosed herein may be performed in a sterile environment.

Reinforcing materials include, but are not limited to, bone reinforcing mixtures (such as bone cement mixtures, bone void fillers, epoxies, glues and similar adhesives), orthopedic wires, stainless-steel rods, metal pins, and other similar devices. An apparatus may be used for the repair of bones that have weakened or fractured due to any of the bone diseases including, but not limited to osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, scoliosis, and other similar diseases.

Embodiments of the apparatus may be used for delivering reinforcing materials to a bone void that has been prepared in a bone using, for example, the disclosed techniques. Although some of the figures show the weakened or fractured bone as a femur, those skilled in the art will recognize that the disclosed apparatus and methods can be used for delivering reinforcing materials to other bones, such as the tibia, fibula, humerus, ulna, radius, metatarsals, metacarpals, phalanx, phalanges, ribs, spine, vertebrae, clavicle and other bones and still be within the scope and spirit of the disclosed embodiments.

Figure 1:
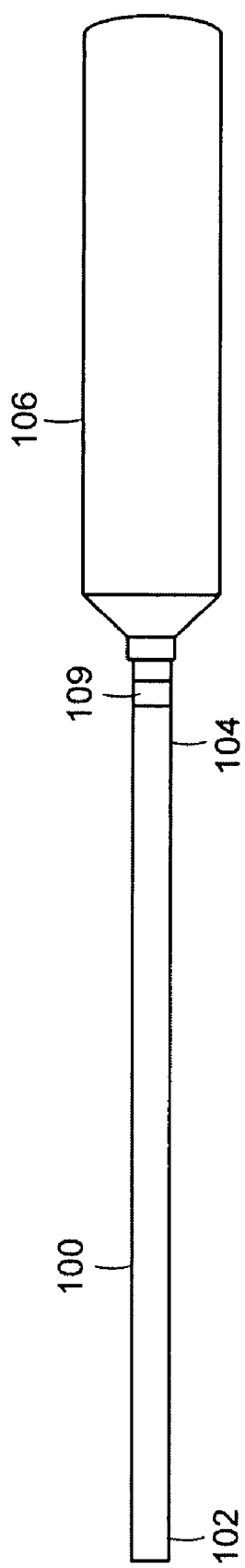
FIG. 1 shows a perspective view of an illustrative embodiment of a catheter having a balloon in an inflated state.
Figure 3:
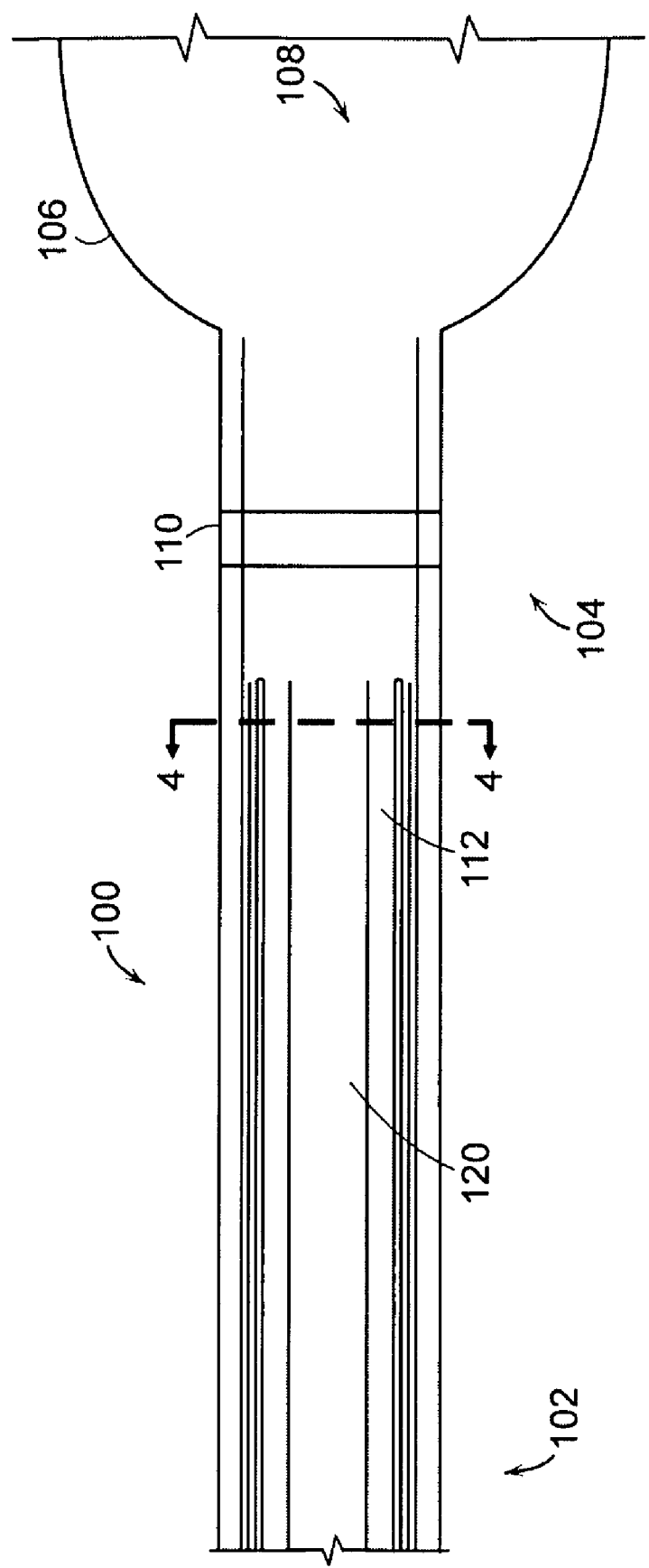
FIG. 3 shows a cross-sectional view of an illustrative embodiment of a catheter.

As shown in FIG. 1 and FIG. 3, a flexible tube is a catheter 100 having an elongated shaft with a proximal end 102, a distal end 104, and a longitudinal axis therebetween. The distal end 104 of the catheter 100 has a balloon portion 106 that inflates and deflates. In an embodiment, the balloon 106 may be round, flat, cylindrical, oval, rectangular or another shape. In an embodiment, a glue 108, such as UV-activated glue, is used to inflate and deflate the balloon 106. A separation area 109 is located at the junction between the balloon 106 and the catheter 100. The separation area 109 may also be an illumination band 110. When activated, the illumination band 110 causes light to cure glue 108 located in the catheter within the illumination band 110, as will be described further below. The illumination band 110 may include light guides 112 which transmit light of the proper frequency to the illumination band 110.

Figure 4:
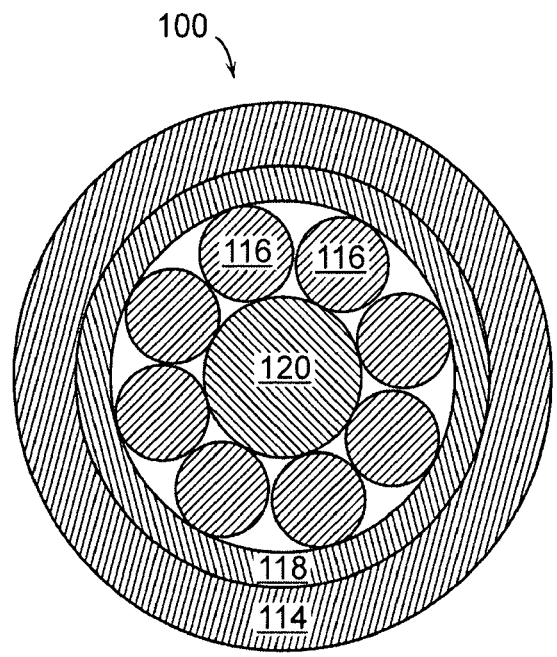
FIG. 4 shows a cross-sectional view of the catheter taken along line 4-4 of FIG. 3.
Figure 5:
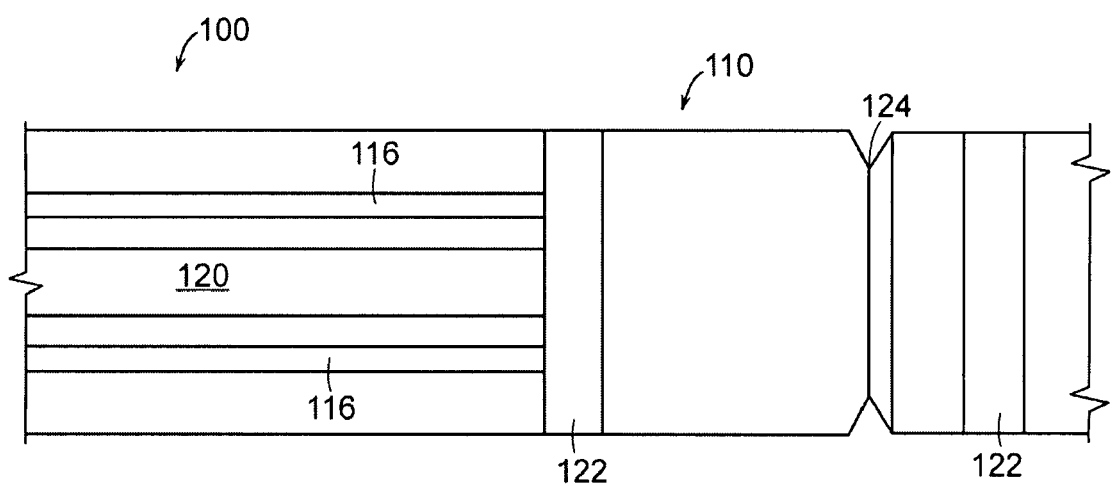
FIG. 5 shows a cross-sectional view of an illustrative embodiment of a catheter.

As shown in the embodiment depicted in FIG. 4, the catheter 100 includes a catheter wall 114, illumination fibers 116, an illumination ring 118 for holding together the illumination fibers 116, and an inner lumen 120 through which the glue 108 is introduced. In an embodiment, it may be desirable for the balloon to separate from the catheter, allowing the balloon to remain in the bone and the catheter to be more easily removed. For example, as shown in the embodiment depicted in FIG. 5, the catheter 100 includes two fused joints 122 and a pre-stressed notch 124 which facilitate a separation of the balloon 106 from the catheter 100, as will be described further below.

The balloon portion of the catheter may be located and inflated at any location along the length of the catheter. The catheter may engage the tubular balloon in such a way as to allow for an open communication channel. The ability to inflate and deflate the balloon ensures that alignment of the plurality of bone fragments for proper healing prior to curing the glue. In an embodiment, inflation of the balloon within the inner lumen of the bone conforms to the shape of the inner bone surface, leading to greater contact area, and provides a custom fit. Those skilled in the art will recognize that a balloon can be formed of a pliable, resilient, conformable, and strong material, including but not limited to urethane, polyethylene terephthalate, nylon elastomer and other similar polymers.

In an embodiment, a catheter may be constructed in a "Y" shape having two arms extending from a longer base. The longer base of the Y shaped catheter is inserted into the bone. A first upper arm of the Y shape engages a syringe. A second upper arm of the Y shape engages a light source. An optical taper may be used and is located between the light source and the catheter. In an embodiment, an outside circumference of the catheter ranges from about 3 French to about 8 French. Using a catheter of about 3 French to about 8 French, results in an inflated diameter of the balloon of about 2 mm to about 30 mm inflated diameter, as appropriate for the internal lumen of the bone. Not all embodiments are intended to be limited in this respect and some embodiments may include a catheter having an outside circumference of less than 3 French or greater than 8 French.

In an embodiment, the catheter can be constructed of illumination materials resulting in a light transmittable fiber catheter, which would not require illumination fibers or light guides.

In an embodiment, an elongated flexible tube having at least one lumen, capable of receiving a fluid from both ends, extends through a flexible bone fitting portion. The flexible tube may also be screwed into a bone via a screw-thread portion. In an embodiment, the elongated flexible tube is a thin catheter. In an embodiment, the elongated flexible tube is a balloon catheter.

The infusion catheter connects the light guides to the light source and precludes inadvertent or early activation of the light source (e.g., prior to the correct positioning and desired infusion amount of UV curable glue). The activation of the light source cures the glue resulting in the affixing of the balloon in the expanded shape. A cure may refer to any chemical, physical, and/or mechanical transformation that allows a composition to progress from a form (e.g., flowable form) that allows it to be delivered through the catheter, into a more permanent (e.g., cured) form for final use in vivo. For example, "curable" can refer to uncured composition, having the potential to be cured in vivo (as by catalysis or the application of a suitable energy source), as well as to a composition in the process of curing (e.g., a composition formed at the time of delivery by the concurrent mixing of a plurality of composition components). The activation of the light source that is connected to the light guides within the balloon causes a complete cure of the reinforcing material to the point where the composition has been finally shaped for its intended use. Activation of the glue does not require a change in shape post activation; there is not shrinking or swelling of the glue after curing.

Once the balloon catheter is positioned, the balloon can be inflated or deflated until the bone is brought to a proper orientation. The balloon is expanded from a deflated state to an inflated state using a UV cured epoxy where a syringe of UV curable epoxy is attached to the luer end of the catheter. The balloon is considered to be in an inflated state when the balloon has a greater volume than when the balloon was in a deflated state. The balloon need not be maximally inflated for the balloon to be considered to be in an inflated state. The balloon withstands high pressure during and after inflation. Inflatable non-conforming balloons are typically capable of withstanding about 400 PSI to about 1000 PSI filled with a UV curable material. The UV curable material becomes a rigid orthopedic fixator capable of holding bone in approximation to effect healing. When the balloon is subjected to internal pressures, the balloon inflates into a cross-sectional shape, which can be circular, oval, disk or similar shapes. The balloon material is flexible, but relatively inelastic so there is minimal radial expansion upon the inflation beyond the pre-defined shape.

Figure 2:
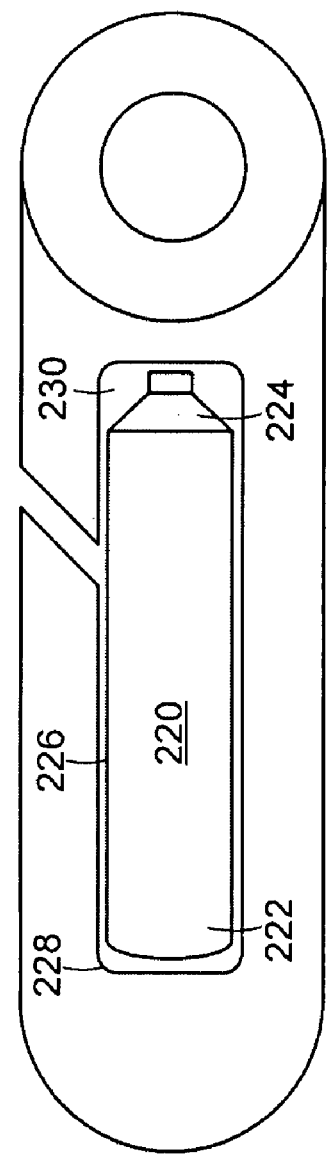
FIG. 2 shows a cross-sectional view of an illustrative embodiment of a balloon in a bone.

In an embodiment, the balloon is designed to evenly contact the wall of the cavity in the bone. For example, as depicted in the embodiment of FIG. 2, the pre-defined shape of a balloon 220 may be an elongated cylinder. The balloon 220 has two ends 222, 224 and a surface 226 therebetween.

The surface 226 of the balloon 220 is substantially even and/or smooth and substantially mates with a wall 228 of a cavity 230 in the bone. The balloon's surface 226 may not be entirely smooth and may have some small bumps or convexity/concavity along its length. In some embodiments, there are no major protuberances jutting out from the surface 226 of the balloon 220. The balloon may be designed to remain within the cavity of the bone and not protrude through any holes or cracks in the bone. In an embodiment, the balloon's outer surface may be flush with the wall of the cavity and when the balloon is inflated, the balloon's outer surface may contact the wall of the cavity along at least a portion of the balloon's surface area. In an embodiment, when the balloon is inflated, a majority or all of the balloon's outer surface does not contact the wall of the cavity and does not extend through any holes or cracks in the bone.

In an embodiment, the balloon may be contoured to fit inside a cavity in a particularly shaped bone. The balloon may be shaped to fit inside a particularly shaped cavity in a bone. In an embodiment, the balloon may be shaped to fit entirely within the cavity of the bone and not protrude out of the cavity through any holes or cracks in the wall of the cavity of the bone.

Upon inflation to higher internal pressures, the balloon assumes a normal cross section. The balloon shape is suitable for balloons formed of polyethylene terephthalate (PET) and similar materials which are not readily heat settable. In an embodiment, the inflation of the balloon within an inner lumen of the bone provides for an even dispersion of radial force. Some balloons may be capable of withstanding more than about 1000 PSI or less than about 400 PSI, as not all embodiments are intended to be limited in that respect.

In an embodiment, the balloon has a diameter of about 5 mm and a length of about 55 mm±4 mm. The length of the balloon may be approximately 44 mm±3.5 mm, 30 mm±3 mm or any other length greater than, equal to or less than about 55 mm, about 40 mm, or about 30 mm and may have any other margin of error, and the diameter of the balloon may be any size, as not all of the present embodiments are intended to be limited in these respects.

The balloon catheter includes a plurality of inner delivery lumens extending outward through a sidewall of the balloon portion and ending in a plurality of passageways that act as delivery surfaces for the delivery of the bone reinforcing mixture. The plurality of passageways may reside anywhere along the length of the balloon portion of the balloon catheter, for example, along the entire length of the balloon portion. The distal end of the balloon catheter may include a radiopaque marker, band, or tip which ensure easy visualization by fluoroscopy during catheter manipulation. The proximal end of the flexible tube may be attached to any adhesive system known in the art to which the bone reinforcing mixture has been placed. Examples of adhesive systems include, but are not limited to, caulking gun type systems, syringe systems, bag systems that contain the bone reinforcing material where the delivery of the bone reinforcing material is controlled using a tube clamp or any other restrictor valve.

The balloon catheter includes a light source path, such as a fiber, that runs down the length of the catheter, either inside the lumen, or on the outside of the catheter, and is able to cure the bone reinforcing mixture once it has been released from the plurality of passageways. When the reinforcing material in the balloon catheter is cured using a light source, light is delivered to cause the glue to cure. Curing a balloon catheter using a light source path uses curing compounds which remain stable until activated by light. The compounds do not require any weighing or mixing prior to application. In operation, radiant energy from a UV light source may be absorbed and converted to chemical energy quickly so that curing happens almost instantaneously. Since curing occurs immediately upon light striking the curing compounds, any substrates will not experience a temperature change or only a brief, superficial temperature change and reaction is not considered exothermic.

In an embodiment, a syringe has a control mechanism to regulate the flow of the glue. The control mechanism of the syringe allows the glue to flow into the catheter and can stop the flow if desired. The syringe makes direct contact to control the directional flow of the glue, and the direction of flow of the glue instantaneously changes within the catheter in response to a change in the direction of the syringe.

In an embodiment, the delivery syringe does not allow light to penetrate the outer surface of the syringe. Having an opaque syringe ensures that the reinforcing material contained in the syringe is not exposed to light and will not cure in the syringe. The delivery syringe delivers an epoxy or glue to the balloon through the catheter. The epoxy is of a liquid consistency, as measured in Centipoise (cP), the unit of dynamic viscosity, so the epoxy can be infused from the syringe into the catheter and into the balloon. Because the epoxy has a liquid consistency and is viscous, the epoxy can be delivered using low pressure delivery and high pressure delivery is not required, but may be used.

After activating the light source, the light is delivered throughout the epoxy in the balloon. By activating the light source, the photocurable material contained in the balloon hardens inside the balloon.

The bone reinforcing mixture may be a natural or synthetic material for strengthening, replacing, or reinforcing of bones or bone tissue. Bone reinforcing mixtures include glues, adhesives, cements, hard tissue replacement polymers, natural coral, hydroxyapatite, beta-tricalcium phosphate, and various other biomaterials known in the art for strengthening, replacing or reinforcing bones. As inert materials, bone reinforcing mixtures can be incorporated into surrounding tissue or gradually replaced by original tissue. Those skilled in the art will recognize that numerous bone reinforcing mixtures known in the art are within the spirit and scope of the presently disclosed embodiments.

The electromagnetic spectrum is the range of all possible electromagnetic radiation. The electromagnetic spectrum of an object is the frequency range of electromagnetic radiation that it emits, reflects, or transmits. The electromagnetic spectrum extends from just below the frequencies used for modern radio (at the long-wavelength end) to gamma radiation (at the short-wavelength end), covering wavelengths from thousands of kilometers down to fractions of the size of an atom. Ultraviolet (UV) light wavelength ranges from about 1 nm to about 380 nm, and can be subdivided into the following categories: near UV (380-200 nm wavelength; abbreviated NUV), far or vacuum UV (200-10 nm; abbreviated FUV or VUV), and extreme UV (1-31 nm; abbreviated EUV or XUV). Similarly, visible light has a wavelength spectrum of between about 380 to about 780 nm.

Light Cured Materials (LCMs) utilize energy provided by ultraviolet (UV) or visible light. Being very energetic, UV light can break chemical bonds, making molecules unusually reactive or ionizing them, in general changing their mutual behavior. In an embodiment, a light emitted by a light source reacts with a photoinitiator sensitive to UV light or visible light. Photoinitiators provide important curing mechanisms for addition polymerization.

Using a UV light, the reinforcing material ensures there is no or minimal thermal egress and that the thermal egress may not be long in duration. More specifically, there is no chemical composition or mixing of materials. The introduction of light starts the photoinitiator and the glue hardens. Once the light is introduced, the material inside the balloon hardens and the materials inside are affixed in place. Until the light is introduced, the bone placement is not disturbed or rushed as there is no hardening of a glue until the light is introduced, the balloon may be inflated or deflated due to the viscosity of the glue. The glue may be infused or removed from the balloon due to the low viscosity of the material. In an embodiment, the viscosity of the reinforcing material is less than approximately 1000 cP. Not all embodiments are intended to be limited in this respect and some embodiments may include reinforcing materials having a viscosity exactly equal to or greater than 1000 cP.

Different light cured materials use photoinitiators sensitive to different ranges of UV and visible light. For example, visible blue light may be useful to the curing process as it allows materials to be cured between substrates that block UV light but transmit visible light (e.g., plastics). Visible light increases the cure speed of light cured materials since a greater portion of the electromagnetic spectrum is available as useful energy. Further, visible light penetrates through light cured materials to a greater depth-enhancing cure depth. The light cured materials cure in such a way that is sufficient to hold a bone in the correct orientation. More specifically, the ability to inflate, set, adjust, orient bones, and the resulting union of the bone are available prior to hardening the glue. Examples of light cured materials include those commercially available from Loctite of Henkel Corporation, located in Rocky Hill, Conn.

In an embodiment, a liquid adhesive such as a cationic epoxy having a cationic photo-initiator is used. A pre-activated epoxy exhibits a very low shrink rate. To activate, a UV light in about 245 nm to about 365 nm range is applied to an epoxy and starts a cure reaction. Once the cure reaction is started, that reaction continues to completion (e.g., even in the dark).

In an embodiment, the reinforcing material is a bioabsorbable epoxy so the hardened epoxy is absorbed into the body over time. In an embodiment, the reinforcing material is cured by chemical activation or thermal activation. Chemical activation includes but is limited to water or other liquids. In an embodiment, the reinforcing material is a drying adhesive which has a polymer dissolved in a solvent such that as the solvent evaporates, the adhesive hardens. In an embodiment, the reinforcing material is a hot or thermoplastic adhesive such that as the adhesive cools, the adhesive hardens. The reinforcing material is not limited to the embodiments described herein and may be any material that reinforces the bone. Some materials may require or be enhanced by curing via any means, such as UV or visible light, heat, and/or addition or removal of a chemical or substance, may utilize any outside or internal processes to cure the material, or may not require curing.

In an embodiment, the bone reinforcing mixture is a light cure adhesive (or UV adhesive). A benefit of ultraviolet (UV) curing is that it is a cure-on-demand process and that adhesives may be free of solvents and include environmentally friendly resins that cure in seconds upon exposure to long wave UV light or visible light. In an embodiment, the UV adhesive is a single-component, solvent-free adhesive that will not cure until a UV light engages the adhesive, and when that occurs, the adhesive will cure in seconds to form a complete bond with a shear strength. Visible light penetrates through the epoxy to a greater depth. Since the visible light penetrates through the epoxy, curing of the material increases as a greater portion of the electromagnetic spectrum is available as useful energy. In this way, light cured materials utilize energy provided by ultraviolet light or visible light to start a curing process. Light emitted by a source reacts with a photoinitiator sensitive to UV light or to visible light. Visible light allows materials to be cured between substrates that block UV light but transmits visible light. Using the UV light to cure the reinforcing material assists in holding broken bones in place, filling of the balloon, and viewing under a C arm imaging system.

Those skilled in the art will recognize that some light cured materials may be activated by UV light, visible light, x-rays, gamma rays, microwaves, radio waves, long waves or any light having a wavelength less than about 1 nm, between about 1 nm and about 380 nm, between about 380 nm and about 780 nm, or greater than 780 nm, as not all embodiments are intended to be limited in that respect.

Figure 24:
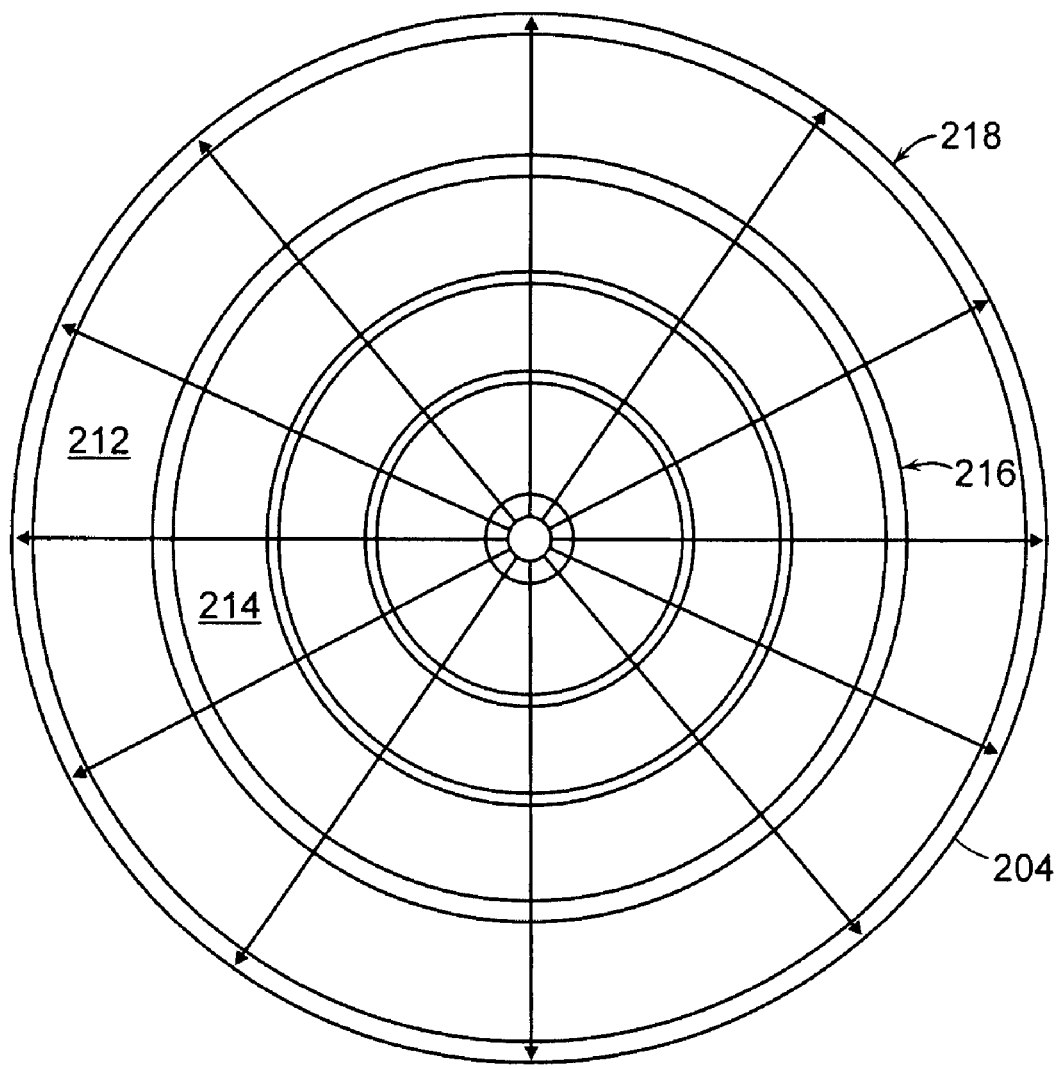
FIG. 24 shows a cross-sectional view of an illustrative embodiment of an internal support structure of a balloon.

Several epoxies known in the art are suitable for use as bone reinforcing materials and vary in viscosity, cure times, and hardness (durometer or shore) when fully cured. A durometer of a material indicates the hardness of the material, defined as the material's resistance to permanent indentation. Depending on the amount of resultant support that is necessary for a given bone fracture, a specific durometer UV adhesive may be chosen. Alternately, multiple UV adhesives having varying durometers may be chosen for the repair of a bone fracture and be within the scope and spirit of the presently disclosed embodiments. The durometer of a material may be altered to achieve either greater rigidity or a more malleable result. As shown in FIG. 24, the shore or durometer of the epoxies may also be varied in a layer-by-layer approach to achieve a softer more malleable outer layer or a rigid internal structure. The shore or durometer may also be altered to ensure the interface between the glue and the bone is flexible similar to natural shock absorption.

The mechanical properties of the epoxies may dictate using methods/measures that are typical for high-strength and high-impact materials including but not limited to, tensile strength and tensile modulus, tensile strength tests, ultimate modulus, Poisson's ratio, hardness measurements like Vickers and Charpy Impact which measures yield strength and toughness.

In an embodiment, the epoxy has an elastic modulus of about 0.1 to about 50 GPa, preferably about 1 to about 10 GPa. Cranial-facial bones have an elastic modulus of about 20 GPa, while plexiglass (PMMA, i.e. bone cement) has an elastic modulus of about 1 to about 2 GPa. Typical epoxies have an elastic modulus in the range of about 1 to about 3 GPa, but nano-modified epoxies can have about a 3-5 fold or more increase over the original epoxy with only a few percent loading of carbon nanotubes, clay, mica, and other structures.

In an embodiment, carbon nanotubes (CNTs) are added to the reinforcing material to increase the strength of the glue. Carbon nanotubes are an allotrope of carbon that take the form of cylindrical carbon molecules and have novel strength properties. Carbon nanotubes exhibit extraordinary strength. Nanotubes are members of the fullerene structural family, which also includes buckyballs. Whereas buckyballs are spherical in shape, a nanotube is cylindrical with at least one end typically capped with a hemisphere of the buckyball structure. Nanotubes are composed entirely of sp2 bonds, similar to those of graphite. This bonding structure, which is stronger than the sp3 bonds found in diamond, provides the molecules with their unique strength. Nanotubes naturally align themselves into "ropes" held together by Van der Waals forces. Single walled nanotubes or multi-walled nanotubes may be used to strengthen the reinforcing materials.

In an embodiment, glue is infused through a lumen in the catheter to expand the balloon to position the bone in a healing orientation. To establish the healing orientation, the balloon inflates until the bones move into an aligned orientation. Orientation of the bones may be done without any visualization of the process or using x-ray or a fluoroscope. A C arm imaging system is a fluoroscope that may allow movement or manipulation of the fluoroscope to rotate around tissue while viewing. Other techniques can be used for monitoring or inspecting the delivery or use of the balloon such as magnetic resonance imaging (MRI), ultrasound imaging, x-ray fluoroscopy, Fourier transform infrared spectroscopy, ultraviolet or visible spectroscopy. The balloon is composed of non ferromagnetic materials and, thus, is compatible with MRI.

Once the glue is hardened, the glue has the appropriate tensile strength, yield, elongation, and other properties to ensure a good bonding of the bone-to-bone repair and maintain strength for healing bone for at least about six weeks. An intramedullary pin or rod is created to hold the bone in a proper healing orientation. The implantable intramedullary rod or pin is capable of being inserted into the bone without driving or insertion force. In an embodiment, the glue mixture has a viscosity of about cP 1000 or less. A contrast material could be added to the glue mixture without significantly increasing the viscosity. Contrast material including, but not limited to, barium sulfate, tantalum, or other contrast materials known in the art. In this way, the glue mixture may be used with a smaller lumen during delivery.

Many glues have a specific cure time dependant upon time and temperature after which the glue enters the plastic region. The disclosed glues cure instantaneously upon activation of a light source allowing a desired amount of glue in a precise location that can cure once struck by incident light.

Figures 6, 7:
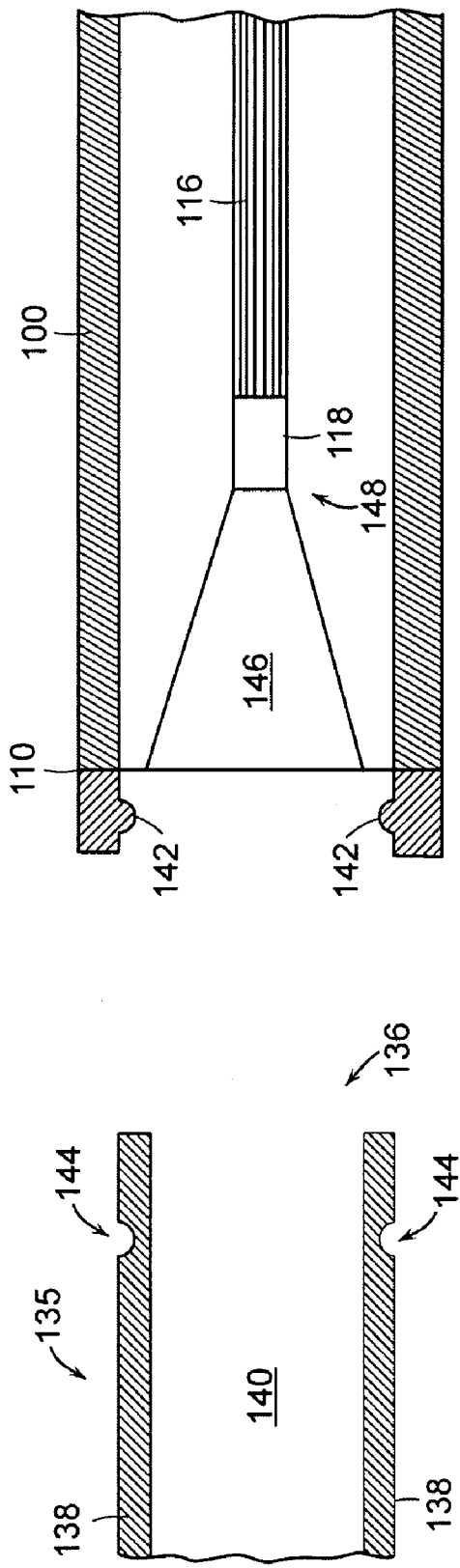
FIG. 6 shows a cross-sectional view of an illustrative embodiment of a catheter having an optical taper.
FIG. 7 shows a cross-sectional view of an illustrative embodiment of a catheter having an optical taper.

In an embodiment, a plurality of light guides engage the light source. In an embodiment, the light guide is a flexible light pipe. The light guide directs light from a light source to the balloon catheter. Because the light source is larger than the diameter of the catheter, a light taper is used to direct the light. As shown in the embodiments depicted in FIG. 6 and FIG. 7, an optical taper 146 may be used for focusing the light from a light source into a smaller catheter 135. In an embodiment, the optical taper 146 is a shaped bundle of optical fibers 116 having a light source that is concentrated at a proximal end 148. As shown in the embodiment of FIG. 7, the catheter also includes a taper holder 137, a light shield 139, a fiber boss 141, a handle 143, illumination bundles 145 having diameters, for example, of about 0.5 mm, about 0.75 mm, about 1.0 mm, about 1.25 mm and/or about 1.5 mm, and a polyimide sheathing 147.

In an embodiment, an optical taper is a single or "multi-element" rod of optical fibers. When a single or multi-element rod is tapered, the resulting optical characteristic of the rod changes to reduce the Numerical Aperture (NA) of the normal end, while maintaining the original Numerical Aperture at the tapered end. The Numerical Aperture of an optical system is a dimensionless number that characterizes the range of angles over which the system can accept or emit light. The amount of change is a ratio of the diameters. When light enters the small end of a taper at a full acceptance angle, the emerging beam at the other end may be collimated as compared to the original range of entry angles. In an embodiment, a catheter has an interface with an optical taper. In an embodiment, the optical taper engages the catheter and is for a single use and disposable. In an embodiment, the optical taper engages the light source and may be used for multiple procedures.

In an embodiment, using an optical taper shapes a concentration of a light beam at the proximal end of the catheter. A disposable section of catheter fibers may be aligned to the taper to improve quality. An optical taper also may provide an appropriate mating point for a disposable piece. One advantage of using an optical taper is that the design of a catheter is simpler because small optical fibers are aligned under a larger optical taper. Since the small optical fibers are aligned under a larger optical taper, alignment is not as important.

A plurality of illumination fibers may be collected by mechanical connectors including, but not limited to, a metallic ring, a polymer ring using glue or similar structures. After the fibers are bound together, the fibers may be cut in an even manner. The light fibers may be polished smooth to assist in pointing light illumination. In an embodiment, the optical taper is mounted adjacent to a light fiber bundle with a tapered end that may be in contact with polished ends of the fibers.

One or more radiopaque markers may be placed on the catheter and/or the balloon. In an embodiment, the radiopaque marker is located at the transition point between the proximal end of the balloon and the distal end of the catheter. The radiopaque marker, using radiopaque material such as barium sulfate, tantalum, or other materials known to increase radiopacity, allows the medical professional to view the distal end of the catheter using fluoroscopy techniques. The radiopaque material provides visibility during inflation to determine the precise positioning of the balloon and/or catheter during placement and inflation. The radiopaque material permits visualization of voids created by air entrapped in the balloon. The radiopaque material permits visualization to preclude the balloon from misengaging or not meeting the bone due to improper inflation to maintain a uniform balloon/bone interface. Once the correct positioning of the balloon and/or catheter is determined, the proximal end of the catheter may be attached to a caulking gun type adhesive system that contains a bone reinforcing mixture.

One or more radiopaque markers on the proximal end and distal end of the balloon and/or catheter may be used to determine the position of the balloon and/or catheter within the bone to ensure correct location of the balloon through the use of an x-ray or fluoroscope. As the balloon is inflated, the multiple sections of bones are brought into a healing orientation and in a stable configuration. If the bone is in the healing orientation, illumination is provided via illumination fibers within the balloon and/or catheter. In an embodiment, a plurality of illumination fibers are used to provide sufficient light to cure the reinforcing material in the bone.

After the reinforcing material in the balloon is cured, such as by using the illumination fibers, an illumination band located, for example, at the balloon/catheter junction may be activated causing light to cure the epoxy located in the catheter within the illumination band. The illumination band is located adjacent to the proximal end of the balloon at the junction between the catheter and the balloon. The illumination band extends around the catheter and has a stress concentrator. The stress concentrator may be a notch, groove, channel or similar structure that concentrates stress in the illumination band. The stress concentrator of the illumination band may be notched, scored, indented, pre-weakened or pre-stressed to direct separation of the balloon from the catheter under specific torsional load. A delivery catheter may use light guides composed of silica, silicon, or polymer materials that transmit light of the proper frequency to the illumination band.

In an embodiment, the proximal end of the balloon may contain glue that is hardened to form a separation area. The separation area ensures that there are no glue leaks from the catheter and/or the balloon. The separation area seals the catheter and/or balloon and removes the delivery catheter by making a break at a known or predetermined site (e.g., a separation area). The separation area is located where the distal end of the catheter meets the proximal end of the balloon because the glue in the balloon is hardened after activation of the illumination band. The separation area may be various lengths and up to about an inch long. When torque is applied to the catheter, the catheter separates from the balloon. Twisting the catheter creates a torque sufficient in the separation area to break the catheter from the balloon. The twisting creates a sufficient shear to break the residual glue and create a clean separation of the catheter/balloon interface. Because the reinforcing mixture in the separation area has been cured and hardened by the illumination band, no reinforcing mixture can leak into the body from the catheter and/or the balloon.

Figure 8:
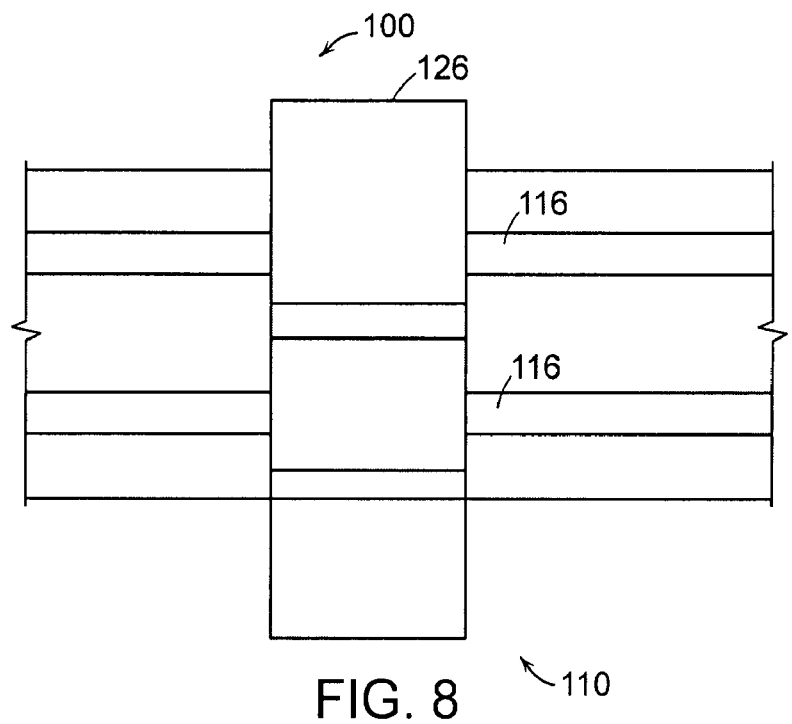
FIG. 8 shows a cross-sectional view of an illustrative embodiment of an illumination band area of a catheter.

For example, as shown in the embodiment depicted in FIG. 6, the illumination band 110 is connected to a light guide 136. The light guide 136 may include a coating 138 surrounding a light guide transmission area 140. The light guide 136 may be removably attached to the catheter 100 using balls 142 which mate with sockets 144. In an embodiment, safety measures prevent accidental or inadvertent illumination. The illumination band is activated by a separate switch which is the active process that the user takes to connect the light to be delivered. Having a distinct switch to activate the illumination band may help to prevent inadvertent delivery of light from the light source to cure the reinforcing material. In an embodiment, such as the embodiment depicted in FIG. 8, the illumination band 110 may have a switch which is a section 126 of the catheter that can be offset by lateral, vertical or horizontal movement. When the section 126 is moved to an offset position, such as is depicted in FIG. 8, the illumination fibers 116 move out of electrical connection with one another on either side of the section 126 and the illumination band 110 is deactivated.

Figure 9:
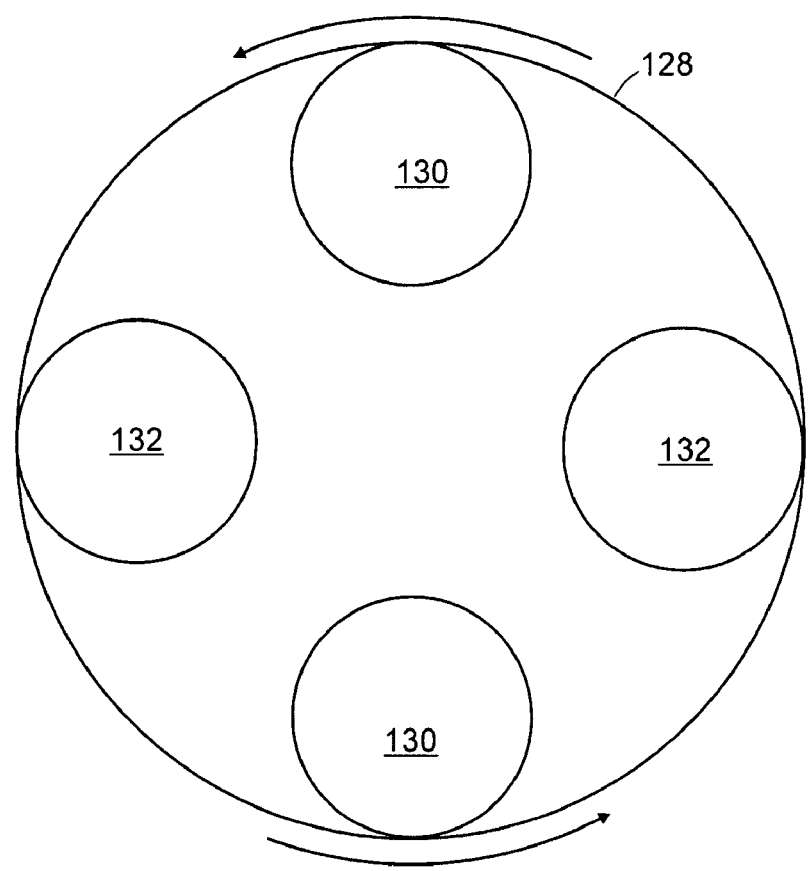
FIG. 9 shows a cross-sectional view of an illustrative embodiment of a switch for an illumination band area of a catheter.

In an embodiment, such as the embodiment depicted in FIG. 9, the switch is a mating device 128 such as a rotating band or rotating fuse that is rotated to activate the illumination band causing illumination on the reinforcing material within the catheter to cure the area adjacent to the illumination band. The mating device 128 may have different connectors 130, 132, such that when the mating device is rotated in a first position, the electrical connectors 132 contact the illumination fibers illuminating the illumination band and when the mating device is rotated, for example, by 90 degrees, into a second position, insulating connectors 130 contact illumination fibers preventing illumination of the illumination band. In an embodiment, such as the embodiment depicted in FIG. 10, the switch is a rotating fuse 134 that is rotated to illuminate the illumination band.

Once the illumination band is activated, a section of the infusion catheter is sealed with the UV curable epoxy proximal and distal to the illumination band. The activation of the illumination band seals the most proximal end of the balloon, seals the distal end of the catheter, and ensures that there is a "hard seal" of the glue at the illumination band allowing no glue to leak from the balloon or the catheter.

In an embodiment, the catheter is cut to separate the balloon from the catheter. A device slides over the catheter and allows a right angle scissor to descend through the catheter and make a cut. The location of the cut may be determined by using a fluoroscope or an x-ray. In an embodiment, the cut location is at the terminal end of the introduction site where the catheter meets the balloon.

In an embodiment, a fracture repair process reinforces a weakened or fractured bone without exposing the bone through a traditional surgical incision (e.g., greater than about 10 mm). The presently disclosed embodiments use a minimally invasive approach by making a minor incision to gain access. Minimally invasive refers to surgical means, such as microsurgical, endoscopic or arthroscopic surgical means, that can be accomplished with minimal disruption of the pertinent musculature, for instance, without the need for open access to the tissue injury site or through minimal incisions. Minimally invasive procedures are often accomplished by the use of visualization such as fiber optic or microscopic visualization, and provide a post-operative recovery time that is substantially less than the recovery time that accompanies the corresponding open surgical approach.

Some of the presently disclosed embodiments are minimally invasive and minimize the cutting of surrounding tissue while implanting a bone fixator within the intramedullary cavity. By restoring and preserving bone structure, some of the presently disclosed embodiments permit additional future treatment options. Benefits of minimally invasive procedures include causing less trauma because there is minimal blood loss, a reduction in surgery and anesthetized time, shortened hospitalization, and an easier and more rapid recovery.

In practice, an incision may be made at the proximal end or distal end of the fractured bone to reveal the bone surface. A medical professional accesses a bone. The medical professional makes an incision through the skin to expose the bone. Once the bone is exposed, it may be necessary to retract some muscles and tissues that may be in view of the bone. Penetration through the compact layer (cortical bone), the spongy layer (cancellous bone) and a portion of the medullary cavity of the bone may be accomplished by any method known in the art and be within the spirit and scope of the presently disclosed embodiments.

The access hole may be a minor drill hole with a diameter of about 3 mm to about 10 mm. A bone drill, awl or other medical device is used to gain access through the compact layer, the spongy layer and a portion of the medullary cavity. The location of the bone penetration site may be at, proximal or distal to the location of the weakened or fractured bone. In using a drill bit, it is desirable for the drill bit to be applied at an angle other than 90° to the bone, for example, at an angle of about 20° to about 45°. The drill bit may be aimed toward the crack line of the weakened area in the bone.

As shown in the embodiments of FIG. 11 and FIGS. 14-16, a guidewire 150 is introduced into the bone via the incision (not shown) and placed between the two sections 182, 184 of bone to cross a bone fracture 186. The guidewire 150 is delivered into the lumen 188 of the bone and crosses the location of the break so that the guidewire 150 spans multiple sections of bone 182, 184. After introducing the guidewire 150, a balloon portion 162, which is constructed and arranged to accommodate the guidewire 150, is delivered over the guidewire 150 to the site of the fracture 186 and spans at least two sections 182, 184 of the bone. Once the balloon portion 162 is in place, the guidewire 150 may be removed. In an embodiment, the balloon portion 162 may be introduced to the surgical site by placing it within the confines of a flexible tube (not shown) and, in turn, delivering the flexible tube to the site of the fracture. By advancing the balloon catheter forward and pulling back on the flexible tube the balloon catheter may be exposed at the location of the fracture. The balloon portion crosses a fracture in a minimally invasive manner.

As shown in the embodiment of FIG. 1, a balloon catheter 152 may be an off-center tube balloon. The balloon catheter 152 may include a guidewire lumen 154 though which the guidewire 150 extends as well as an infusional lumen 156 at least partially surrounded by balloon light guides 158 and at least partially surrounded by illumination band light guides 160. The illumination band light guides lead into an illumination band 164. A balloon portion 164 of the balloon catheter 152 is located at a distal end of the balloon catheter 152. The balloon portion 164 may include a lumen 166 through which the guidewire 150 or another instrument may pass and radiopaque bands 168 at the most distal end so that a surgeon or user may know the location of the tip of the balloon catheter 152. In addition the balloon portion 164 may include a tubular balloon 170 and stents 172 encapsulated therein.

Figure 17:
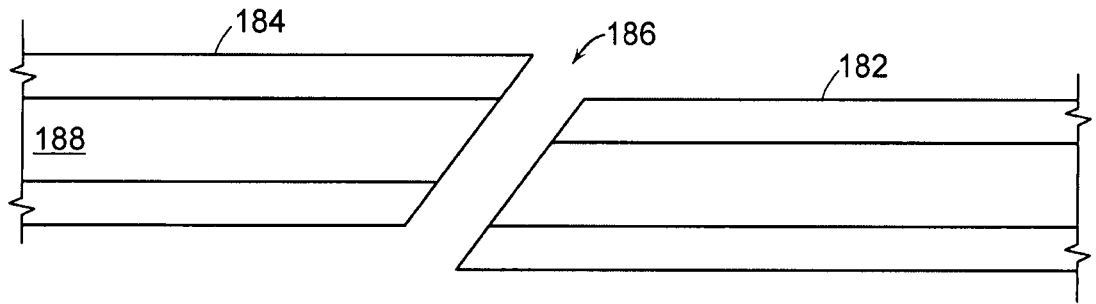
FIG. 17 shows a cross-sectional view of an illustrative embodiment of a fractured bone.
Figure 18:
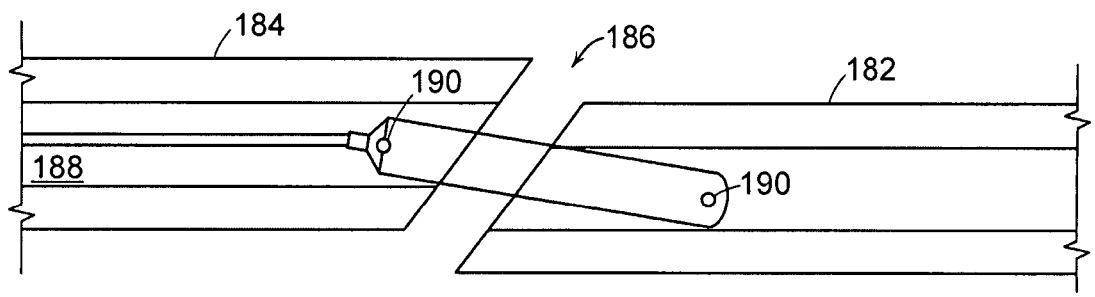
FIG. 18 shows a cross-sectional view of an illustrative embodiment of a balloon catheter inserted in a fractured bone.
Figure 19:
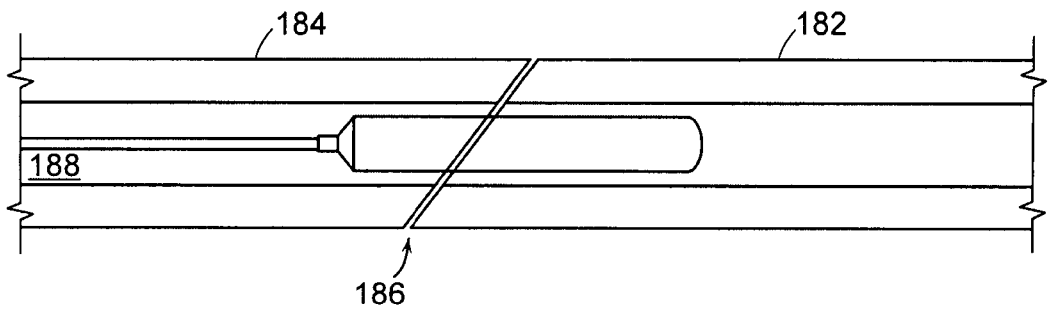
FIG. 19 shows a cross-sectional view of an illustrative embodiment a balloon catheter in an inflated state in a bone.

As shown in the embodiments of FIGS. 17-19, a balloon portion 162 is introduced into the bone via the incision (not shown) and placed between two sections 182, 184 of bone to cross the bone fracture 186. The balloon portion 162 is delivered into the lumen 188 of the bone and crosses the location of the break so that the balloon portion 162 spans multiple sections of bone 182, 184. The location of the balloon portion may be determined using a marker which are detectable from the outside or the inside of the bone. For example, as shown in the embodiment depicted in FIG. 18, radiopaque markers 190, which are visible from outside of the body using x-ray or other detection means, are located on the distal and proximal ends of the balloon portion 162 to help align and position the balloon portion 162. After introduction to the bone, the balloon portion 162 is manipulated to span at least two sections 182, 184 of the bone. Once the balloon portion 162 is in place, the balloon portion 162 is inflated, for example by filling the balloon with a UV cured glue. As the balloon is inflated, the fracture 186 is reduced. Once orientation of the bone sections 182, 184 are confirmed to be in a desired position, the glue may be fixed, such as by illumination with a UV emitting light source.

The balloon containing the hardened reinforcing mixture may be used as an internal support mandrel in the bone. Other devices (e.g., bone screws, plates, pins, and similar devices) may be screwed into the mandrel to provide support for compression and torsion of other devices. In an embodiment, the internal structure is used as a mandrel support for smaller pieces of a fracture repair since the mandrel allows screws to be drilled into its hardened shape.

In an embodiment, an access hole of the bone is capable of accepting a variety of surgical instruments including, but not limited to, catheters, radial structural members, stents, stent-like devices, cannulas, orthopedic wires, stainless steel rods, metal pins and other devices. For example, a self-expandable device made from a material such as Nitinol wire may be used to provide structure and support for a bone reinforcing mixture that is delivered to the balloon. A flexible tube may be placed through the central hole and the self-expandable device may be collapsed and brought through the flexible tube and positioned within the balloon.

Figure 12:
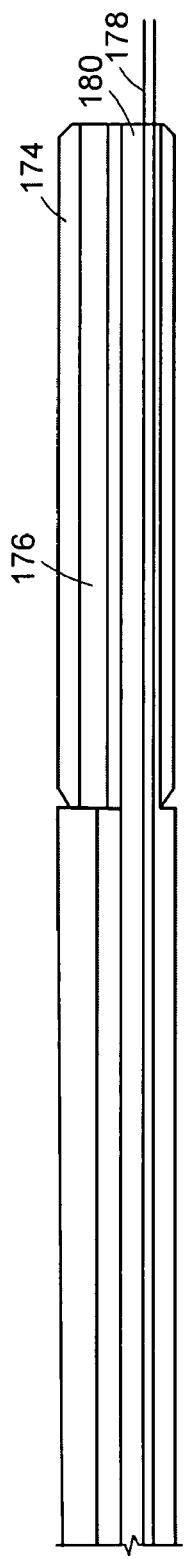
FIG. 12 shows a cross-sectional view of an illustrative embodiment of a balloon catheter in a deflated state.
Figure 13:
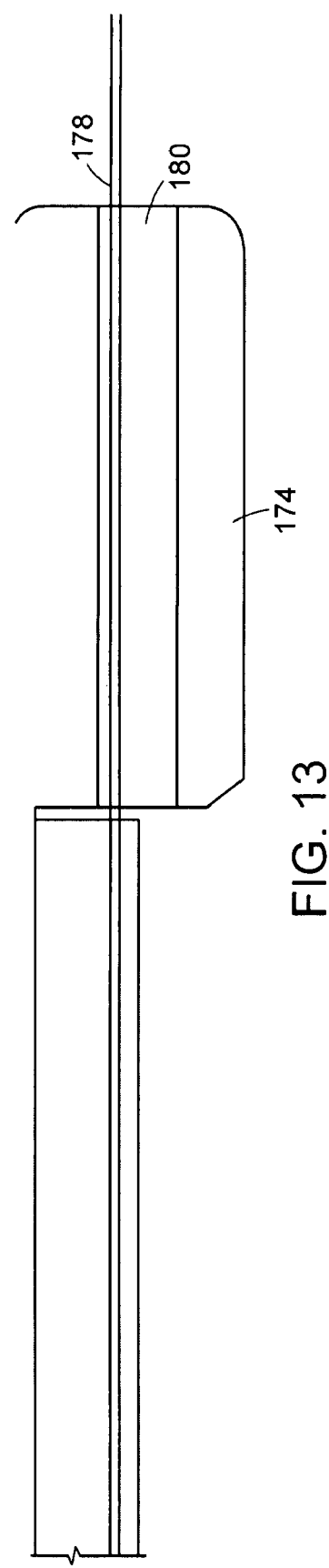
FIG. 13 shows a cross-sectional view of an illustrative embodiment of a balloon catheter in an inflated state.
Figure 14:
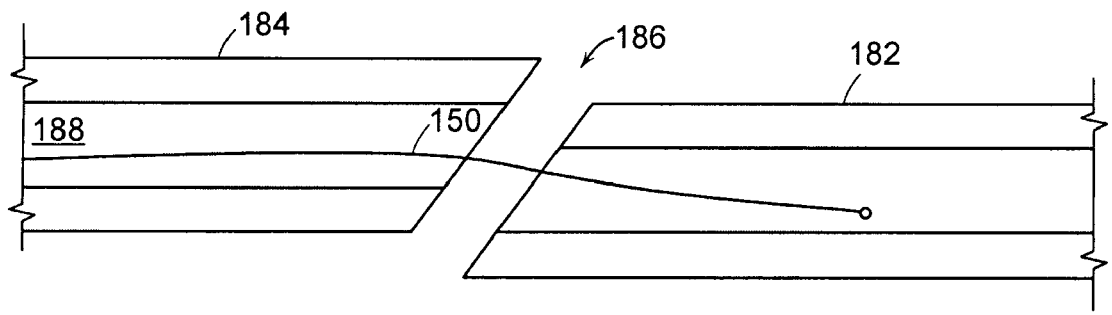
FIG. 14 shows a cross-sectional view of an illustrative embodiment of a fractured bone with a guidewire therein.
Figure 15:
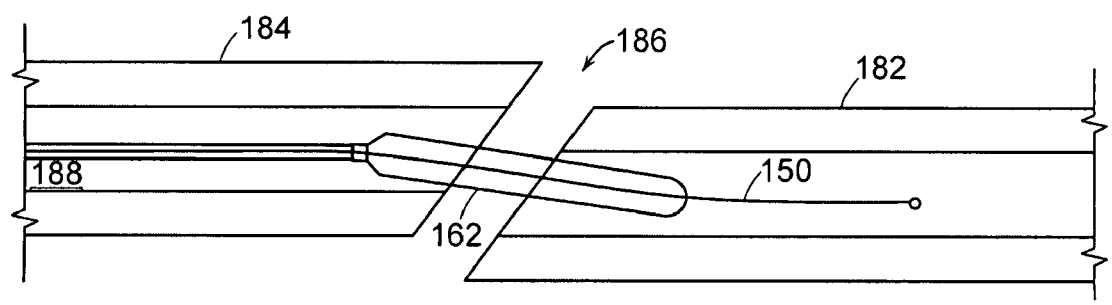
FIG. 15 shows a cross-sectional view of an illustrative embodiment of a bone and a guidewire with a balloon catheter inserted on the guidewire.
Figure 16:
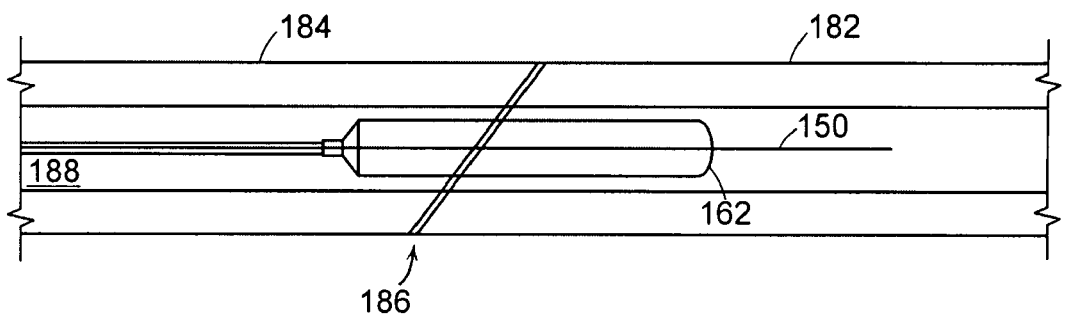
FIG. 16 shows a cross-sectional view of an illustrative embodiment of a bone, a guidewire and a balloon catheter in an inflated state.

FIG. 12 and FIG. 13 show embodiments wherein a flexible tubular or regular balloon 174 has a radial structural member 176. The radial structural member 176 is capable of being expanded within the confines of the balloon and may be held and affixed within the UV curable glue. The radial structural member 176 provides for greater column support and strength to the UV glue structure. In addition the catheters may have a lumen 180 through which a guidewire 178 is inserted.

Figure 27:
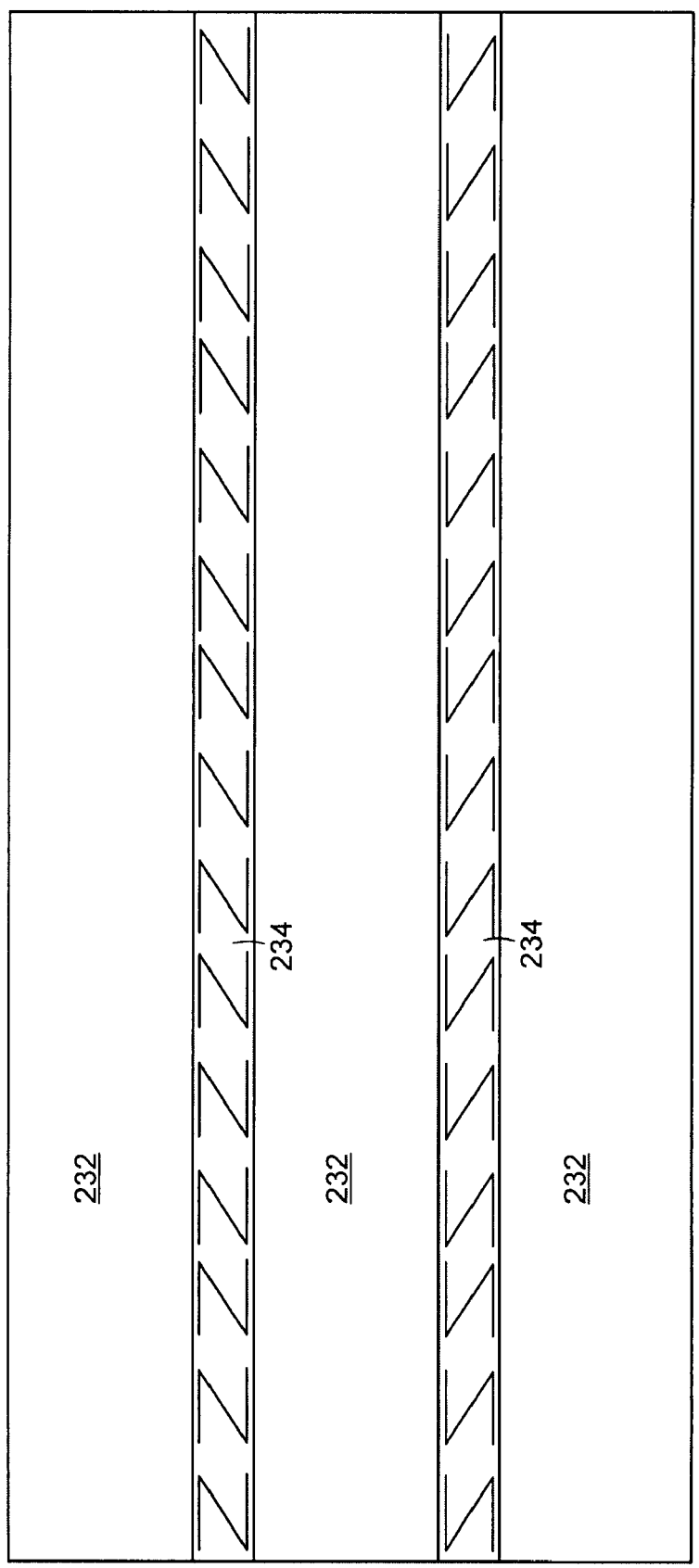
FIG. 27 shows a cross-sectional view of an illustrative embodiment of connector wires and Nitinol plates.
Figure 28:
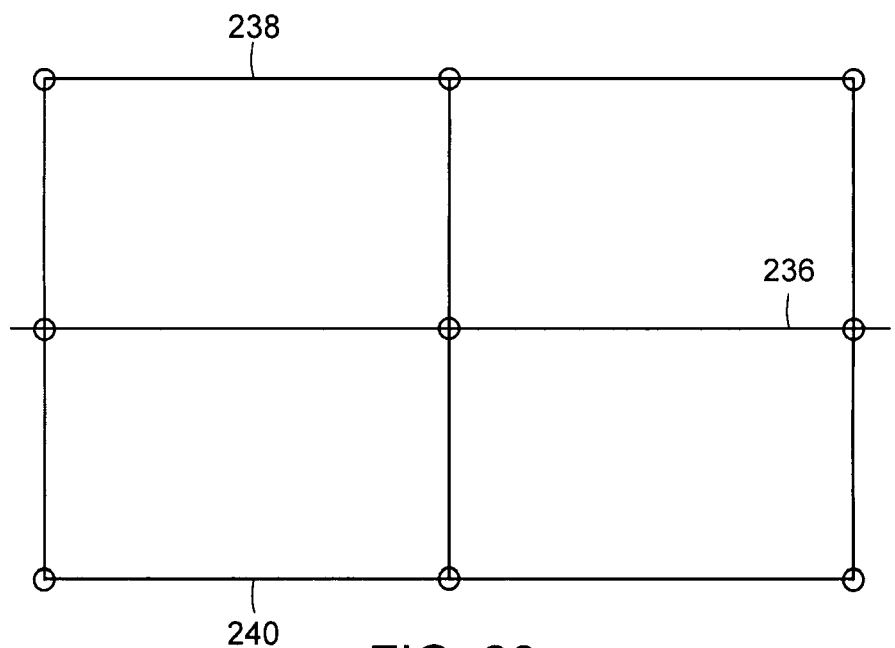
FIG. 28 shows a perspective view of an illustrative embodiment of Nitinol and hinge wires.
Figure 29:
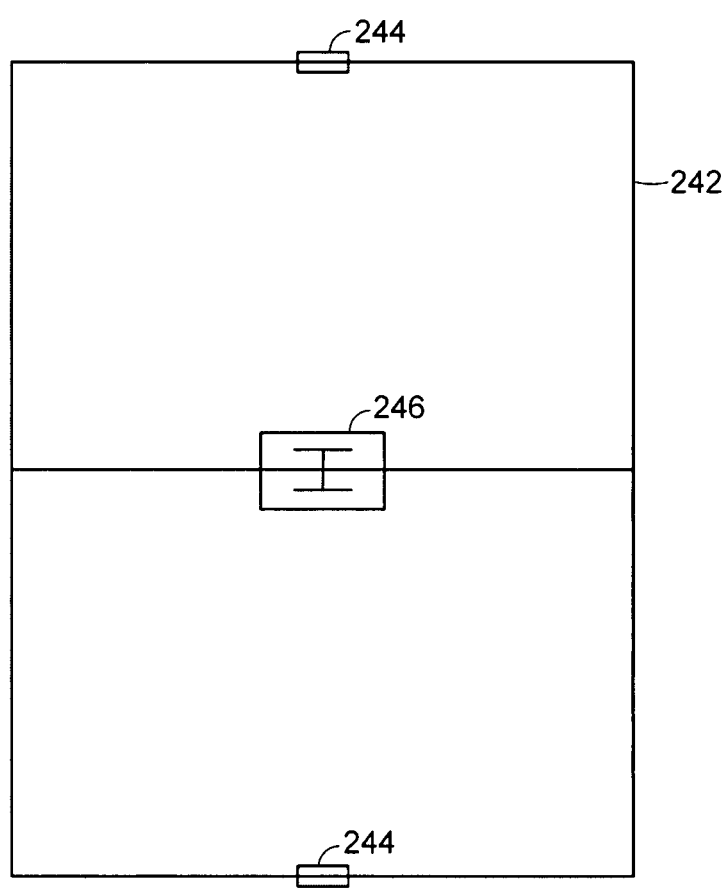
FIG. 29 shows a perspective view of an illustrative embodiment of a plate.
Figure 30:
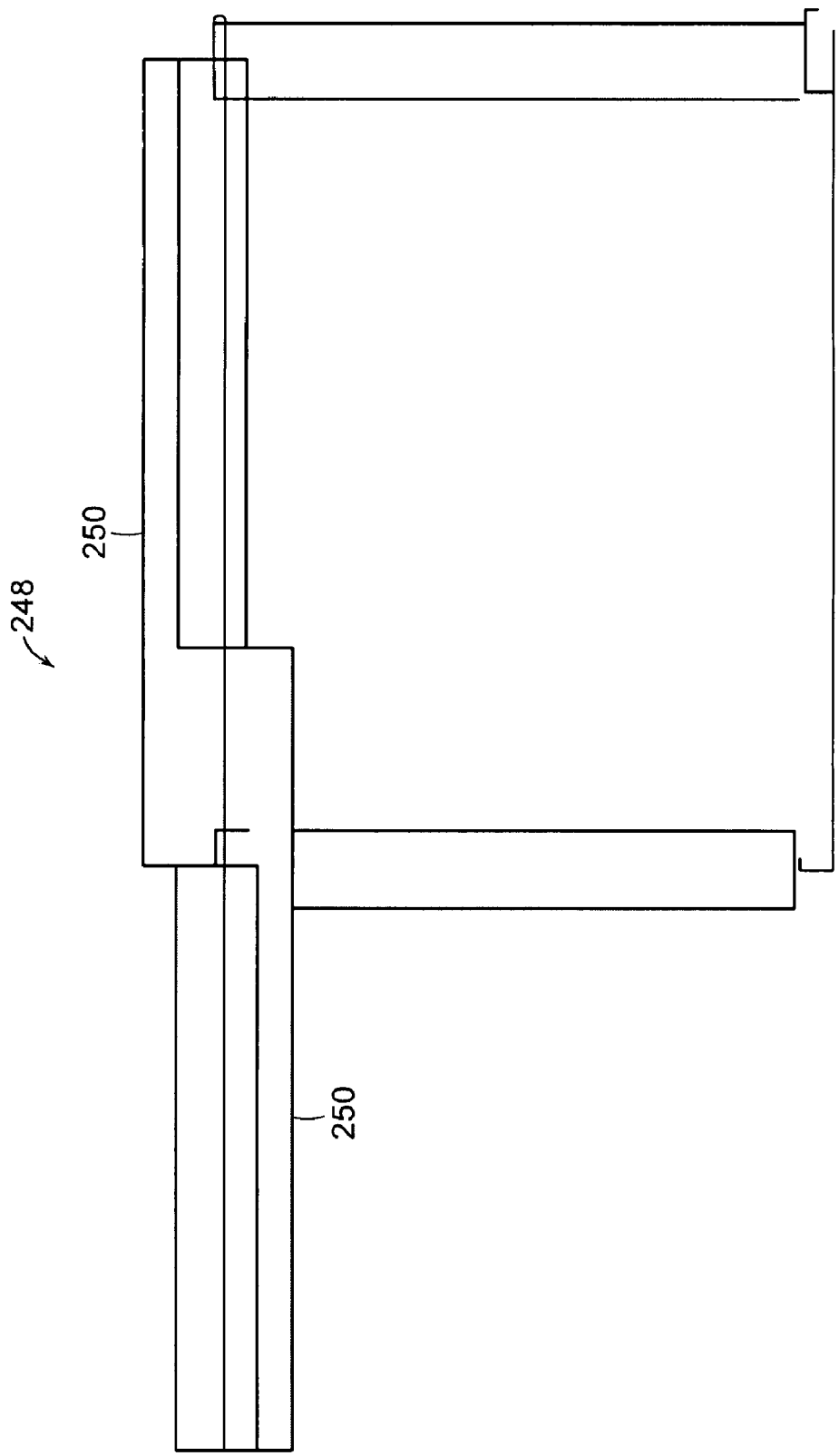
FIG. 30 shows a perspective view of an illustrative embodiment of a frame.

FIGS. 27-30 show various views of balloon catheter embodiments including levered radial structural members and plates. As shown in the embodiment of FIG. 27, Nitinol plates 232 sandwich connector wires 234 therebetween. As shown in the embodiment of FIG. 28 a hinge wire 236 moves in and out of radial structure members where a top Nitinol wire 238 pushes and a bottom Nitinol wire 240 pulls. As shown in the embodiment of FIG. 29, a plate 242 has Nitinol wire attachments 244 and a hinge 246 therebetween. As shown in the embodiment of FIG. 30, upon activation a frame 248 "swings" from a cylinder to an "I" beam construction having connector wires 250.

Figure 25:
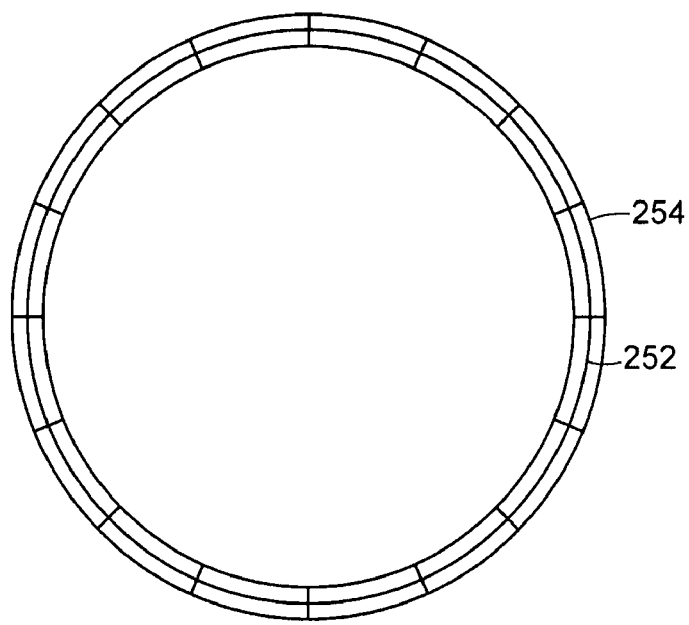
FIG. 25 shows a cross-sectional view of an illustrative embodiment of a stent in a contracted state.
Figure 26:
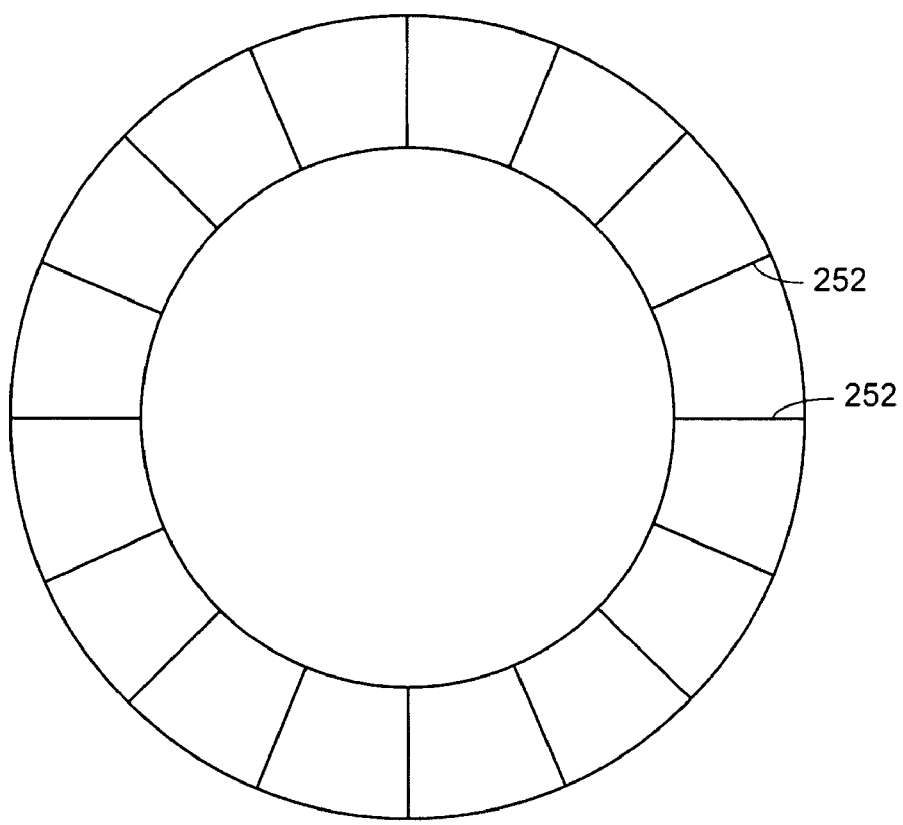
FIG. 26 shows a cross-sectional view of an illustrative embodiment of a stent in an expanded state.

As shown in the embodiments depicted in FIG. 25 and FIG. 26, a radial stent embodiment includes a plurality of vanes 252 that open perpendicular to the outer diameter 254 once expanded. In a deflated (compressed) state, as shown in the embodiment of FIG. 25, the radial stent embodiment is with the vanes 252 lying flat along the wall of the balloon.

The radial structural embodiment includes a plurality of longitudinal plates that are oriented along the circumference and outer surface of the balloon prior to inflation of the balloon. The longitudinal plates are thin and metallic, and may be composed of a memory type metal. In an embodiment, the longitudinal plates are composed of Nitinol.

In a deflated (compressed) configuration, the plurality of longitudinal plates may be located at the distal end of the catheter within the balloon and wrapped around the inner catheter diameter. In the compressed configuration, the plurality of longitudinal plates are adjacent to each other and may abut each other. In an embodiment, the plurality of longitudinal plates may overlap.

As the balloon is inflated, the stent is similarly expanded with the plurality of longitudinal plates moving outward and away from each other. As the balloon continues to inflate, the diameter increases and the orientation of the plurality of longitudinal plates move from being parallel to the catheter, toward being perpendicular to the catheter.

The longitudinal plates of the structural member engage adjacent plates by a series of wires. The wires may be metallic, and may be composed of a memory type metal. In an embodiment, the wires are composed of Nitinol. A lower portion of the plate located closest to the catheter wall engages the wire that is designed to contract, while an upper portion of the plate engages the wire that is designed to expand. The opposing forces of the wires along with the radial expansion and the overlapping layers of the plates cause a window blind effect where the radial structural member opens and becomes a rigid structure inside the balloon.

Figure 20:
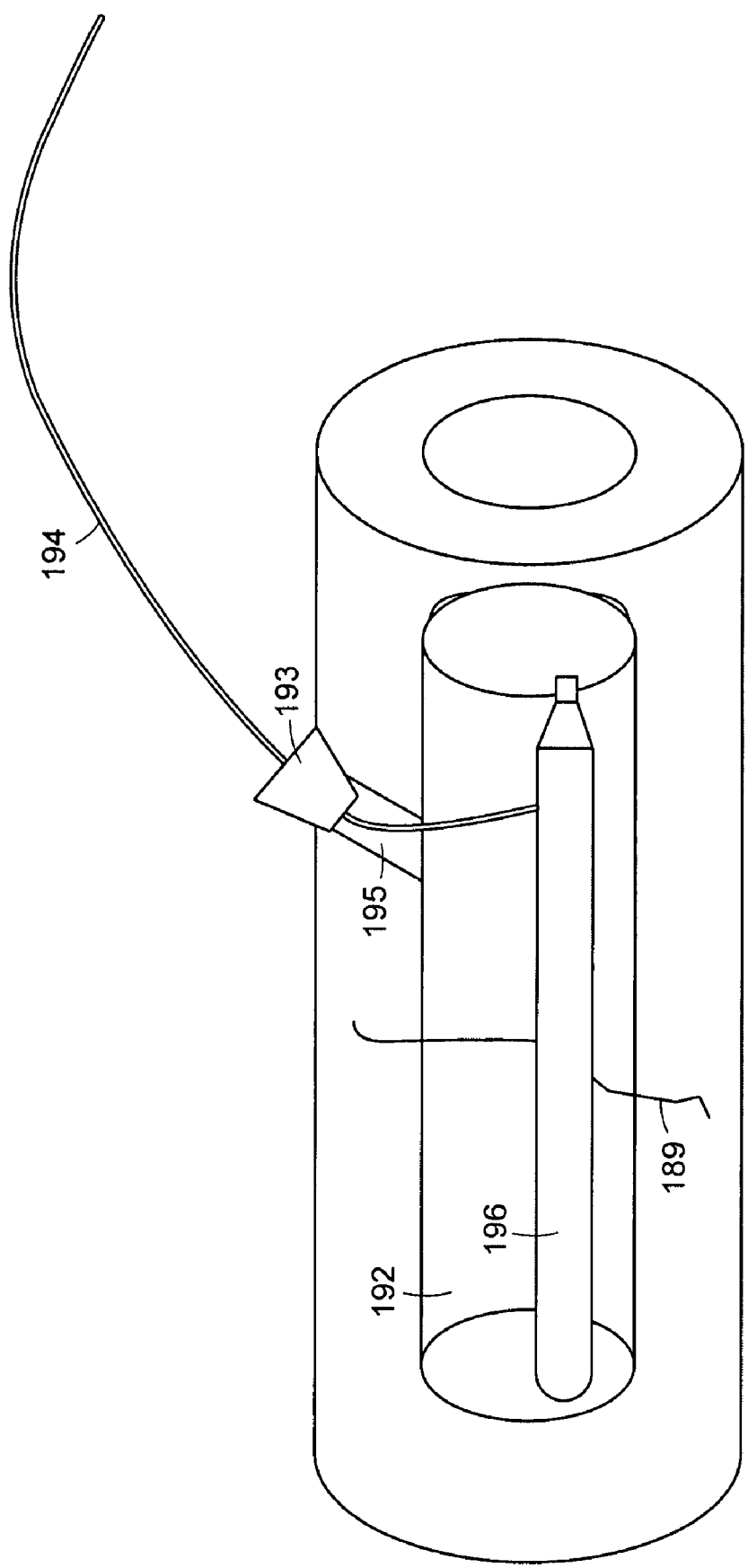
FIG. 20 shows a cross-sectional view of an illustrative embodiment of a balloon in a deflated state in a fractured bone.
Figure 21:
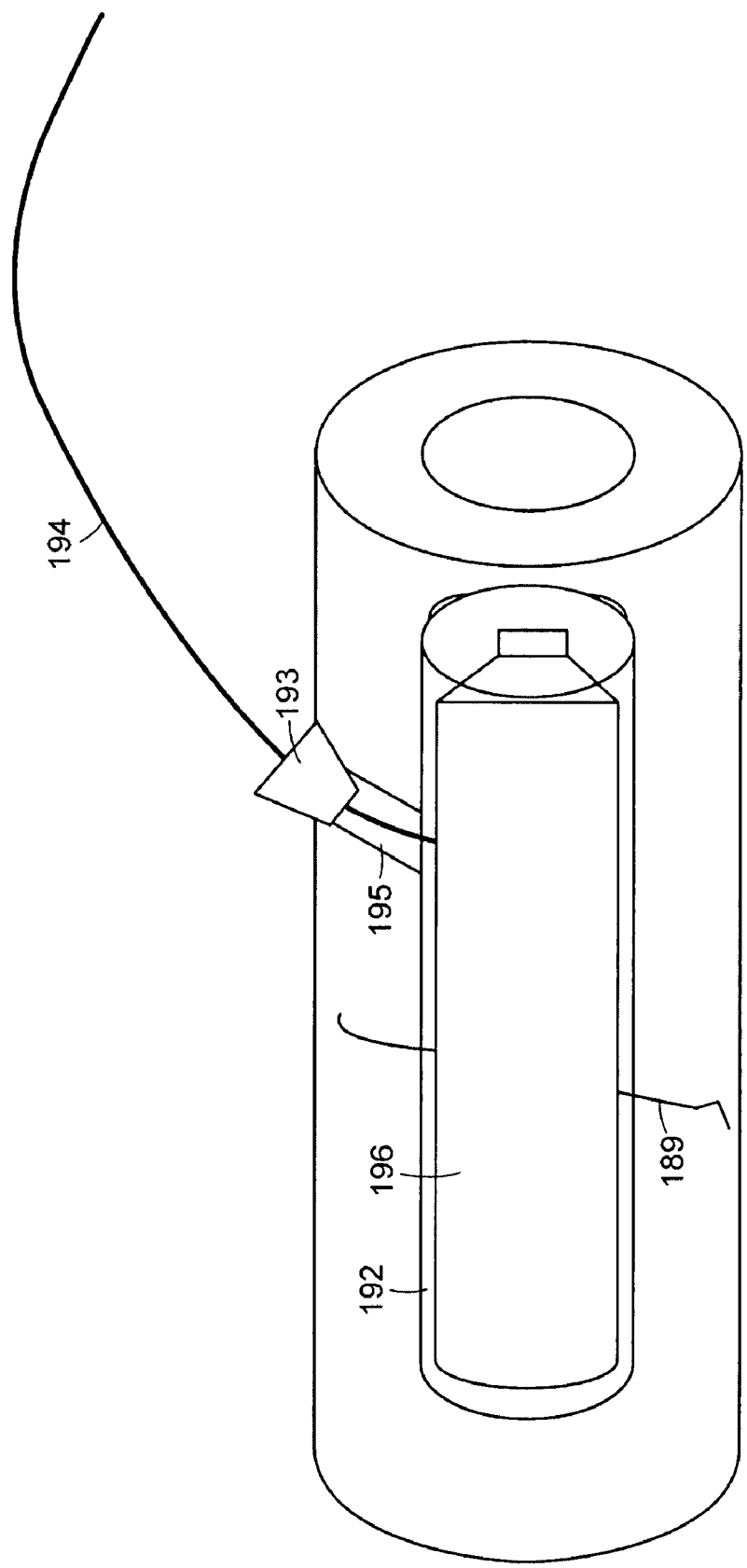
FIG. 21 shows a cross-sectional view of an illustrative embodiment of a balloon in an inflated state in a fractured bone.

As shown in the embodiment of FIG. 20, a deflated balloon is placed within a medullary cavity 192 of a bone having a fracture 189. The balloon catheter is inserted into the bone through a trocar fitting 193 in a hole 195. The trocar fitting may be a high pressure trocar fitting which is installed in the access path. The trocar fitting may seal the chamber, may hold the glue in place prior to activation and may ensure that air voids are removed from the cavity. The medullary cavity 192 may also contain a guidewire 194 for use in guiding and positioning a balloon 196. As shown in the embodiment of FIG. 21 the balloon 196 is inflated by filling the balloon 196 with bone cement. A syringe is used to pack the balloon densely so it is hard upon activation by the light source. It is useful to note that high pressured delivery is not required to inflate the balloon or to move the glue from the glue delivery system to the balloon. When using the syringe delivering the glue, no high pressure is used otherwise the balloon may deflate and the glue would retrograde. If the glue retrogrades, there is not enough suction to pull the administered glue from the balloon.

Figure 22:
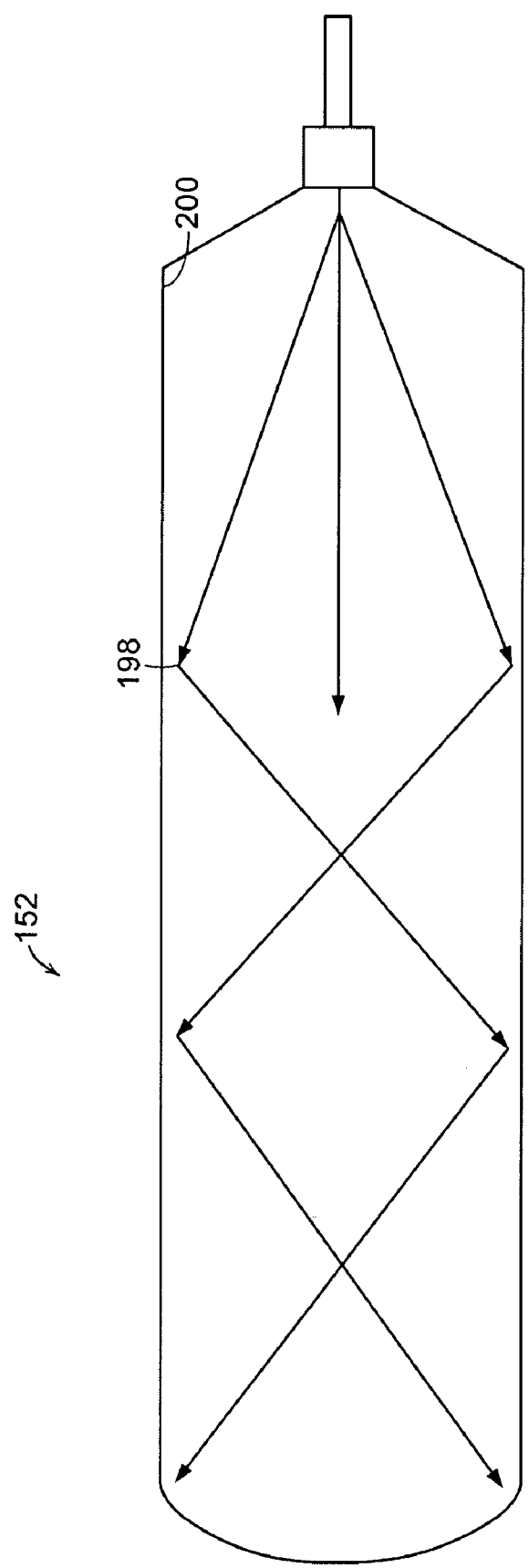
FIG. 22 shows a cross-sectional view of an illustrative embodiment of a balloon.

A balloon catheter may have a wide variety of properties including, but not limited to, fiber type, fiber orientation, and resin matrix of the composite structure. As shown in FIG. 22, the balloon catheter 152 may be inner reflective where a light reflective material 198 on an inner surface 200 of the balloon catheter enhances the reflective properties of light tubes.

Figure 23:
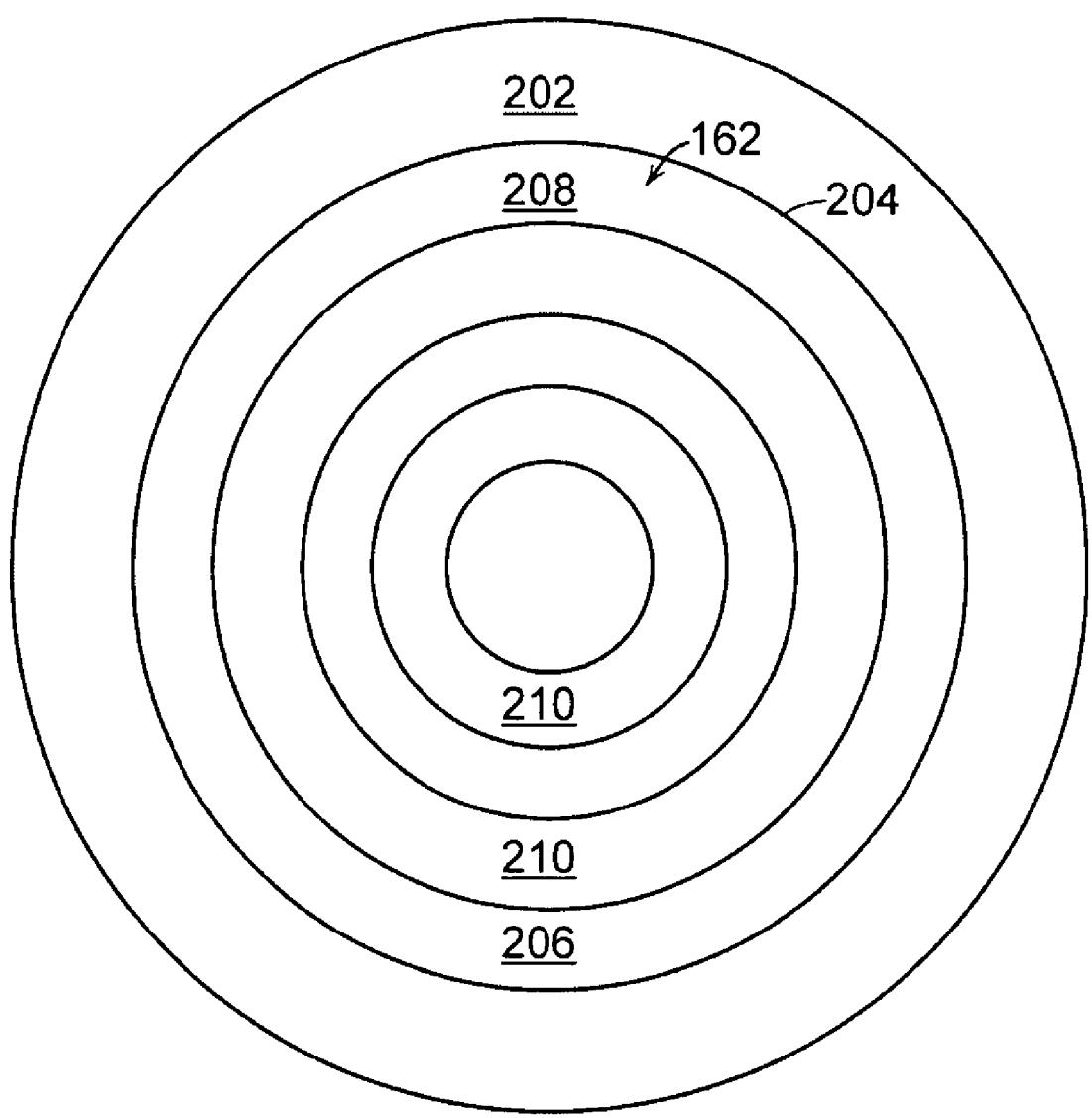
FIG. 23 shows a cross-sectional view of an illustrative embodiment of a balloon in a bone.

The embodiment depicted in FIG. 23 shows a cross section view of a luminal fill having high modulus fiber structure. A bone 202 surrounds an outer surface 204 of the balloon portion 162. A lumen 206 of the balloon portion 162 is filled with a polymer 208. The balloon portion 162 may also include an interlinked concentric ring of high modulus fiber 210. The embodiment depicted in FIG. 24 shows a cross section view of an embodiment of an internal support structure of a balloon. The balloon catheter may contain strong and stiff fibers used for carrying a load imposed on a composite while the resin matrix distributes the load across the fibers. An internal support within the balloon may help create a composite filler that adds rigidity to the balloon and is useful in application for longer bones where greater strength for fixation is desired. In particular, contained within the outer surface 204 of the balloon are circumferential cross strut connectors 212, high wet modulus circumferential supports 214, lower 'wet' media 216, which allows for some miscibility and outward compression, and high 'wet' porous high modulus media 218.

In an embodiment, the catheter may be opaque. The opaque catheter ensures that the glue is not activated by ambient light prior to the desired activation of the light source. Similarly, a syringe may also be opaque to ensure that ambient light and operating room light does not activate the glue prior to the desired activation time. In an embodiment, the glue is preloaded into the opaque syringe where inflow and outflow of the glue is regulated until application of the light is desired to harden the glue.

After a balloon catheter is attached to the delivery system which contains the bone reinforcing mixture, the bone reinforcing mixture is infused through one of the lumens of the balloon catheter. In an embodiment, the bone reinforcing mixture is a UV adhesive which requires a UV light source to cure the adhesive. The balloon portion is then inflated and the UV adhesive is released through the plurality of passageways running along the sidewall of the balloon portion. The UV adhesive may also be released through the inner lumen of the catheter. The UV adhesive is pushed or compressed hydraulically up against the wall of the balloon. The light guides connected to the light source are illuminated which cures the UV adhesive. The balloon portion of the catheter is then slightly deflated followed by infusion of the same or a different UV adhesive delivery system through a different lumen of the balloon catheter. The balloon portion is then re-inflated and the UV adhesive is released through passageways. The UV adhesive is pushed or compressed hydraulically against the UV adhesive that has been previously cured. The UV light guides connected to the light source are illuminated which cures the UV adhesive. The balloon portion of the catheter is then slightly deflated followed by infusion of the same or a different UV adhesive delivery system through a different lumen of the balloon catheter. The balloon is being reinforced from the walls inward creating a shell or layer by layer repair producing a strong, resilient union. The process is repeated until most of the space in the balloon has been filled with UV adhesive. A central space may remain in the balloon which may be filled in order to provide the strength and support to the bone. An optical rod or similar device may be positioned in the central space and turned on or illuminated. An optical rod or similar device can be made of fiber, silica, quartz, sapphire or similar materials. The UV light will then harden the remaining UV adhesive in the balloon. The end of the optical rod may be cut and remain in the balloon to provide increased rigidity.

UV curing adhesives may use ultraviolet light to initiate curing, which allows a bond without heating. Additives may be used with the UV adhesive delivery system, including, but not limited to drugs (for example, antibiotics), proteins (for example, growth factors) or other natural or synthetic additives.

An outer surface of the balloon may be coated with materials such as drugs, bone glue, proteins, growth factors, or other coatings. For example, after a minimally invasive surgical procedure an infection may develop in the patient, requiring the patient to undergo antibiotic treatment. An antibiotic drug may be added to the outer surface of the balloon to prevent or combat a possible infection. Proteins, such as, for example, the bone morphogenic protein or other growth factors have been shown to induce the formation of cartilage and bone. A growth factor may be added to the outer surface of the balloon to help induce the formation of new bone. The lack of thermal egress with these glues in the balloon maintains the effectiveness and stability of the coating.

In an embodiment, the outer surface of the balloon may have ribs, ridges, bumps or other shapes to help the balloon conform to the shape of the cavity. Balloons may be constructed to achieve transit within luminal cavities of bones and to expand, manipulate, and remove obstructions. In this way, the balloon may slide easier within the luminal bodies without coming in contact with surrounding tissue. The balloon may also be designed to be placed in a bone and to grab a fractured bone without any slippage using a textured surface with a variety of shapes such as small ridges or ribs.

In an embodiment, a water soluble glue is applied to the outer surface of the balloon. When the balloon is expanded and engages the moist bone, the water soluble glue on the outer surface of the balloon becomes sticky or tacky and acts as a gripping member to increase the conformal bond of the balloon to the bone. Once the balloon is inflated, the outer surface of the balloon grips the bone forming a mechanical bond as well as a chemical bond. These bonds prevent the potential for a bone slippage. It is useful to note that the water soluble glue may be cured by any light (e.g., UV not required).

In an embodiment, a textured surface may provide one or more ridges that allow grabbing both portions of the bone segments. In an embodiment, ridges are circumferential to the balloon and designed to add more grab to the inflated balloon on contact with the bone. The ridges are also compressive so the ridges fold up on the bone when the balloon is completely inflated. In an embodiment, sand blasted surfacing on the outer surface of the balloon improves the connection and adhesion between the outer surface of the balloon and the inner bone. The surfacing significantly increases the amount of surface area that comes in contact with the bone resulting in a stronger grip.

A two wall balloon has an inner wall and an outer wall making a tube. A radial structural member may be placed inside the tube. A radial structural member is inside the balloon and the epoxy expands the balloon. Then simultaneous with the expansion the radial structural member is being expanded.

In an embodiment, a longer radial structural member extends beyond the distal and proximal ends of the balloon within the intramedullary cavity. When the balloon is expanded, the radial structural member supports beyond and farther than the actual area of the balloon, and the radial structural member provides greater strength to the bone, resulting in a stronger device using a small balloon. Typically, radial structural members are constructed from non-thrombogenic materials of sufficient flexibility (in an unexpanded state) to allow passage through guiding catheters and tortuous vessels. Such radial structural members are typically radiopaque to allow fluoroscopic visualization. Radial structural members may be constructed from stainless steel or titanium, e.g., in the form of an expandable mesh, wire coil, slotted tube, or zigzag design.

In an embodiment, an injectable fixation pin engages a cavity of the bone completely around the intramedullary cavity of the bone. The internal fixation pin is capable of holding and affixing the bone, which removes the need for external casting. A benefit of the internal fixation pin is that bone-on-bone rubbing or chatter at the fracture site is reduced which enhances healing by having about 360 degree radial contact with evenly distributed pressures with the bone over the length of the internal fixation pin. The internal fixation pin securely affixes the bone fragments and minimizes flexure to hold the bone in place. The internal fixation pin is placed within the intramedullary cavity of the bone without a driving force prior to inflation.

In an embodiment, a small access is created in the bone. In bones with marrow, a section of the marrow should be cleared providing access to the cortical bone. Clearing the marrow results in good approximation and force on bone fragments. Next a balloon is inserted. In an embodiment, the balloon is delivered using the force of the catheter to insert the balloon to span the fracture. In an embodiment, a guidewire is delivered to the fracture site and the balloon is delivered over the guidewire to the fracture site. In an embodiment, a balloon is placed in a flexible delivery tube and the balloon and the delivery tube is sent to the fracture site and then the delivery tube is withdrawn, exposing the balloon. In an embodiment, the delivery balloon could be an expandable framework that the balloon uses to expand like that of a molly bolt. A molly bolt could be placed on a flexible rod and the balloon is used to expand the molly bolt resulting in additional structural support.

The balloon is inflated when a UV curable, light activated epoxy is infused through a catheter to the balloon. In an embodiment, the balloon is constructed out of a polyethylene terephthalate (PET) nylon aramet or other non-consumable materials. PET is a thermoplastic polymer resin of the polyester family that is used in synthetic fibers. Depending on its processing and thermal history, PET may exist both as an amorphous and as a semi-crystalline material. Semi-crystalline PET has good strength, ductility, stiffness and hardness. Amorphous PET has better ductility, but less stiffness and hardness. PET can be semi-rigid to rigid, depending on its thickness, and is very lightweight. PET is strong and impact-resistant, naturally colorless and transparent and has good resistance to mineral oils, solvents and acids, but not to bases.

The balloon typically does not have any valves. One benefit of having no valves is that the balloon may be inflated or deflated as much as necessary to assist in the fracture reduction and placement. Another benefit of the balloon having no valves is the efficacy and safety of the device. When there is a separation of epoxies prior to curing, there is a potential for particles to egress. Since, since there is no communication passage of glue to the body there cannot be any leakage of epoxy because all the glue is contained within the balloon. In an embodiment, a permanent seal is created between an implant that is both hardened and affixed prior to the delivery catheter being removed. The balloon may have valves, as all of the embodiments are not intended to be limited in this manner.

In an embodiment, a double wall balloon is used. A double wall balloon is a balloon within a balloon that protects against a rupture of the inner balloon and also keeps the hardened glue mixture from the blood stream. As the outer balloon comes in contact with the rough and surface of the bone, the inner balloon remains in contact with the smooth surface of the polyethylene terephthalate (PET) inner material. Each balloon may be inflated in turn until the desired structure is obtained. Any unused balloons may remain deflated with the cavity of the other inflated balloons. A balloon within a balloon may also allow for precise glue location since there is a variable durometer.

In an embodiment, multiple balloons are inserted together with multiple lumens and at least one inflation lumen for each balloon. The innermost balloon would be infused first and could be infused with the strongest glue having the highest shore or durometer. After the inner balloon is hardened, the next balloon is infused with a glue which may have a variable shore or durometer or the same shore or durometer and then hardened. The process is continued until the lumen is completely filled. If there are extra balloons, they would engage the inner balloons and push against the outer cavity of the balloon. The balloons would still conform to the shape of the bone cavity. In an embodiment, the outer layer could have a lower shore or durometer (i.e. be softer) and provide a shock absorber approach to absorb any pressure impact along the bone interface.

In an embodiment, the inflatable balloon is encapsulated in an expandable metallic tube. The metallic tube may be designed to extend beyond the area of the fracture into a healthy bone. The metallic tube may have up to four or more pre-formed lengths that make up the tube. The tube may be capable of being split and provide a greater longitudinal strength than that of the balloon length. The tube that is contemplated could have some ridges or serrations on the outer surface to engage the bone and grab the surface as it is compressed against the bone to prevent any shifting.

The presently disclosed embodiments can be used to treat a wrist fracture of a radius, an ulna or other wrist and hand bones, resulting in a wrist reduction. The wrist is a collection of many joints and bones that allow use of the hands. The wrist has to be mobile while providing the strength for gripping. The wrist comprises at least eight separate small bones called the carpal bones, which connect the two bones of the forearm, called the radius and the ulna, to the bones of the hand and fingers. The metacarpal bones are the long bones that lie mostly underneath the palm, and they are in turn attached to the phalanges, the bones in the fingers and thumb. The wrist is complicated because every small bone forms a joint with its neighbor. Ligaments connect all the small bones to each other, and to the radius, ulna, and metacarpal bones. A wrist injury, such as falling on the outstretched hand, can damage these ligaments and change the way the bones of the wrist work together. The wrist can be injured in numerous ways. Some injuries seem to be no more than a simple sprain of the wrist when the injury occurs, but problems can develop years later. The joints are covered with articular cartilage that cushions the joints. A more serious injury, such as a fracture of one or more bones of the wrist, can injure the articular cartilage surfaces of the joints and lead to degenerative arthritis.

Distal radius fractures are common injuries that occur at the distal end of the wrist, where the wrist joint lies. The most common form of wrist fracture causes the radius to bend away from the palm. There may be a change in shape of the wrist, which is called the "dinner fork" deformity after its shape.

The most common cause of wrist fractures is when an individual falls on an outstretched hand. In young adults, fracture is the result of moderate to severe force. The risk of injury is increased in patients with osteoporosis and other metabolic bone diseases. In addition, when a fracture of the wrist occurs, the fracture may cause the radius to become short compared to the ulna. The ulna may then get caught when the wrist moves causing pain and restriction of movement.

The presently disclosed embodiments and methods treat a wrist fracture in a minimally invasive manner and can be used for a wrist reduction of any of the bones of the wrist and hands, in particular the radius and ulna.

The presently disclosed embodiments can be used to treat a clavicle fracture, resulting in a clavicle reduction. The clavicle or collar bone is classified as a long bone that makes up part of the shoulder girdle (pectoral girdle). Present methods to affix a broken clavicle are limited. The clavicle is located just below the surface of the skin, so the potential for external fixation including plates and screws is limited. In addition, the lung and the subclavian artery reside below the collar bone so using screws is not an attractive option. Traditional treatment of clavicle fractures is to align the broken bone by putting it in place, provide a sling for the arm and shoulder and pain relief, and to allow the bone to heal itself, monitoring progress with X-rays every week or few weeks. There is no fixation, and the bone segments rejoin as callous formation and bone growth bring the fractured bone segments together. During healing there is much motion at the fracture union because there is not solid union and the callous formation often forms a discontinuity at the fracture site. A discontinuity in the collar bone shape often results from a clavicle fracture.

The presently disclosed embodiments and methods treat a clavicle fracture in a minimally invasive manner and can be used for a clavicle reduction or collar bone reduction. A benefit of using a balloon catheter to repair a collar bone is the repair minimizes post repair misalignment of collar bone. A benefit of using the balloon catheter to repair a clavicle is to resolve the patient's pain during the healing process.

Those skilled in the art will recognize that the disclosed apparatus and methods can be used for delivering reinforcing materials to other bones, such as radius, ulna, clavicle, metacarpals, phalanx, metatarsals, phalanges, tibia, fibula, humerus, spine, ribs, vertebrae, and other bones and still be within the scope and spirit of the disclosed embodiments.

In an embodiment, a balloon catheter having larger sized ends of will cause the bone to be placed in inward compressive loading. The balloon is shaped so a proximal end and a distal end that have an inflated diameter that is larger than a diameter of a middle portion of the balloon. The larger diameters of the balloon are toward the distal end and the proximal end that engage the bone beyond the fracture site. The balloon shaped with larger diameters toward the proximal end and the distal end drives the bone portions on each side of the fracture together. The balloon shaped with larger diameters toward the proximal end and the distal end tries to push the bone portions toward each other to promote healing of the fracture.

In an embodiment, the balloon wall is composed of a plurality of layers. In an embodiment, the balloon wall has three layers so the balloon is tri-layered. An outer layer of the balloon has at least a portion that can absorb moisture and expand, creating a thicker skin. In this mode of loading, the upper skin of the balloon wall is in compression, the lower skin of the balloon wall is in tension and the core layer of the balloon wall is subjected to shear stress. Thus, shear strength and stiffness are important properties of a core layer of the balloon wall. To bend the tri-layered balloon, one layer of the balloon wall is compressed, another layer of the balloon wall is placed in tension, and the core layer of the balloon wall is subjected to shear stress.

In an embodiment, a sound may be used to clear the cavity of the bone of any extraneous material to ensure a conforming fit between the balloon and the cavity, knocking off spicules. In an embodiment, a stent could be attached to the sound and is inserted through the cavity. The stent would remain within the cavity to support the cavity. The balloon would then be placed into the cavity after the stent has already been placed there. In an embodiment, a radial structural member may be located inside a balloon.

For bones with marrow, the medullary material should be cleared from the medullary cavity prior to insertion of the balloon catheter. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris needs to be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. The length of medullary material removed will vary according to the area of weakened portion, but will typically include about 3 cm above and about 3 cm below the weakened portion of the bone. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

After the medullary material has been removed, the apparatus may be positioned at the penetration site. A bone fitting portion is threaded into the penetration site and the flexible tube is inserted through the insertion hole of the bone fitting portion. In an embodiment, the lumen used may be smaller than the expanded diameter of the balloon. The access hole need only to be large enough to be able to insert the diameter of the catheter with the deflated balloon around the catheter. For example, the introduction hole into the bone may have a diameter of about one millimeter to about three millimeters where the subsequent inflation of the balloon can be from about 20 millimeters up to about 300 millimeters, as constrained by the internal diameter of the bone. This leaves results in a minimally invasive procedure to reduce the bone fracture. If desired, reinforcing materials including, but not limited to, flexible orthopedic wires, stainless steel rods, and metal pins may be added to the balloon before the flexible tube is placed in the bone fitting portion. The introduction of reinforcing materials to the balloon may help the bone reinforcing mixture to form a tight union, producing a structure that is strong and resilient.

In its expanded state, the internal fixation device is larger than the access hole that is created in the bone. By expanding from a deflated state to an inflated state in the medullary cavity, the internal fixator provides minimally invasive bone reduction. Inserting a balloon catheter within the medullary canal in a reduced diameter allows the balloon catheter to adapt itself to the contours of the medullary canal. Fixation is achieved along the entire length of the balloon allowing proper positioning at fracture site. Other benefits include: a minimally invasive procedure, no interlocking wires/screws required, minimized fluoroscopy exposure, reduced procedure time, one minimally invasive entry point, thus reducing the risk of infection, as the balloon adapts to the intramedullary canal shape and diameter, a homogeneous fixation of the fracture is achieved and there are no transverse movements at the fracture site, the balloon inflation will reduce the fracture fragments as there is an internal framework to push the fragments on, immediate axial load transfer in-between the fracture fragments contributes to faster callus formation. Using the presently disclosed embodiments, the bone reduction does not require any communicating devices in contact with the skin, so there is less irritation and potential for infection.

In an embodiment, the reinforcing material is pre-formed into a customized shape. A pre-determined shape or mold may be filled with the reinforcing material and the shaped material may be inserted into the body. In an embodiment, the shaped material is further cured using one of the processes described above, such as UV light curing. In an embodiment, the material is partially or completely cured while in the mold and inserted into the body intact.

The devices and methods described herein may be used for a variety of applications, for example, they may be used to provide temporary support to an external splint or to form a plate.

In an embodiment, light is delivered to a first end of the balloon through a first catheter and glue is delivered to the other end (e.g., the second end) of the balloon through a second catheter. In an embodiment, both light and glue are delivered to the same end of the balloon and through separate catheters. In an embodiment, light and glue are delivered to the middle of the balloon through a single catheter. Light and glue may be delivered to the balloon through a single catheter or separate catheters, may be delivered to any location on the balloon (e.g., either end, middle or anywhere therebetween) and may be delivered to the same or different locations as one another, as not all of the present embodiments are intended to be limited in these respects.

Advantages in treating osteoporotic bone and pathological fractures may include minimal entry points which will reduce soft tissue injury and subsequent adhesions and scar formation, benefits of adhesion, ability to apply variable Durometer materials within the lumen capable of changing the characteristics of the epoxies to meet the needs and challenges of the application, high tack and softer materials on the outside of the lumen for bonding with the bone and "shock absorption" on the outer layers and greater strength and rigidity on the inside.

Another advantage of using some of the presently disclosed embodiments may be that there is minimal soft tissue damage that occurs. Soft tissue damage creates callous formations which are considered part of the natural bone healing process. By minimizing the soft tissue damage, subsequent stiffness due to callous formations in and on the tendon is avoided. A small incision is made, through which the pin is driven into the cavity of the bone resulting in good approximation and fixation while there is no need for a cast that is required with traditional k-wire approach. The above identified advantages may result from some of the presently disclosed embodiments and not all embodiments necessarily have these advantages.

U.S. application Ser. No. 11/789,906 entitled "Apparatus and Methods for Reinforcing Bone," filed Apr. 26, 2007, is hereby incorporated herein by reference in its entirety.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus for delivering a reinforcing mixture to a long bone comprising:
   a tube having a proximal end, a distal end, and a longitudinal axis therebetween, wherein the tube has at least one inner lumen for passing a bone reinforcing mixture therethrough;
   a balloon engaging the distal end of the tube, wherein the balloon expands from a substantially deflated state to a substantially inflated state upon the bone reinforcing mixture entering the balloon; and
   at least one light guide extending through the tube into the balloon to guide a light into the balloon to illuminate and cure the bone reinforcing mixture,
   wherein the balloon, when in the inflated state by the bone reinforcing mixture in a cavity of a fractured long bone, aligns bone fragments of the fractured long bone.

2. The apparatus of claim 1 further comprising a light source that provides light to the tube.

3. The apparatus of claim 2 wherein the light source provides an ultraviolet light to the tube.

4. The apparatus of claim 2 wherein the light source provides a visible light to the tube.

5. The apparatus of claim 1 further comprising an optical taper adjacent to the proximal end of the tube to guide light into the tube.

6. The apparatus of claim 1 further comprising a separation area on the distal end of the tube to separate the tube from the balloon.

7. The apparatus of claim 1 further comprising a radiopaque marker on a distal end of the balloon.

8. The apparatus of claim 1 further comprising an outer balloon surrounding the balloon.

9. The apparatus of claim 1 wherein at least a portion of the bone reinforcing mixture is removed from the balloon before curing.

10. The apparatus of claim 1 wherein the balloon inflates as the bone reinforcing mixture enters the balloon under pressure.

11. The apparatus of claim 1 wherein a surface of the balloon is substantially smooth.

12. The apparatus of claim 1 wherein a surface of the balloon is preformed to be contained within the cavity of the long bone.

13. The apparatus of claim 1 wherein the balloon is shaped to substantially conform to a wall of the cavity of the long bone.

14. An apparatus for delivering a reinforcing mixture to a long bone comprising:
   a catheter having a proximal end, a distal end, and a longitudinal axis therebetween, wherein the catheter has at least one inner lumen for passing a reinforcing mixture therethrough;
   a balloon extending from the distal end of the catheter, wherein the balloon begins to expand from a substantially deflated state to a substantially inflated state as the reinforcing mixture enters the balloon;
   at least one light guide extending through the catheter into the balloon to guide a light into the balloon to illuminate and cure the reinforcing mixture; and a junction connecting the catheter to the balloon, wherein the junction concentrates stress applied to the catheter at the junction,
wherein the balloon, when in the inflated state by the reinforcing mixture in a cavity of a fractured long bone, aligns bone fragments of the fractured long bone.

15. The apparatus of claim 14 wherein the junction includes at least one of a notch, a groove and a channel in the catheter.

16. The apparatus of claim 14 wherein the junction includes a pre-weakened area extending substantially around a circumference of the catheter.

17. The apparatus of claim 14 wherein the junction is designed to separate the balloon from the catheter under at least a predetermined load.

18. The apparatus of claim 14 wherein the junction extends less than an inch along the longitudinal axis of the catheter.

19. The apparatus of claim 14 further comprising a light source that provides light to the light guide.

20. The apparatus of claim 19 wherein the light source provides an ultraviolet light.

21. The apparatus of claim 19 further comprising at least one lumen of the catheter for transmitting light from the light source into the balloon.

22. The apparatus of claim 14 further comprising an illumination band located at the junction.

23. A method for reinforcing a long bone comprising:
penetrating the long bone to gain access to a cavity in the long bone;
inserting a balloon connected to a distal end of a catheter into the cavity in the long bone;
infusing a reinforcing mixture into the balloon through at least one lumen of the catheter; and
activating a light source to harden the reinforcing mixture in the balloon.

24. The method of claim 23 further comprising maintaining the balloon entirely within the cavity in the long bone.

25. The method of claim 23 further comprising separating the catheter from the balloon.

26. The method of claim 23 further comprising leaving the balloon in the cavity of the long bone.

27. The method of claim 23 wherein the light source provides an ultraviolet light.

28. The method of claim 23 further comprising inflating the balloon with the reinforcing mixture.

29. The method of claim 23 further comprising deflating the balloon by removing at least a portion of the reinforcing mixture before curing.

30. The method of claim 23 further comprising positioning the balloon with a first portion of the balloon on a first side of a fracture in the long bone and a second portion of the balloon on a second side of the fracture in the long bone.

31. The method of claim 23 further comprising transmitting light from the light source into the balloon through at least one second lumen of the catheter.

32. The method of claim 31 wherein the at least one lumen of the catheter and the at least one second lumen of the catheter are different lumens of the catheter.

33. The method of claim 23 further comprising infusing a second portion of the reinforcing mixture into the balloon catheter through the at least one lumen of the catheter and activating the light source to harden the second portion of the reinforcing mixture in the balloon.

34. A method for reinforcing a long bone comprising:
penetrating the long bone to gain access to a cavity in the long bone;
inserting a balloon into the cavity in the long bone;
introducing a bone reinforcing mixture into the balloon through at least one lumen of a catheter connected to the balloon;
activating a light source connected to at least one light guide extending through the catheter into the balloon to harden the bone reinforcing mixture in the balloon; and
separating the catheter from the balloon at a predetermined site.

35. The method of claim 34 further comprising forming the predetermined site before inserting the balloon into the cavity in the long bone.

36. The method of claim 35 wherein the predetermined site is formed by creating at least one of a notch, a groove and a channel in the catheter.

37. The method of claim 35 wherein the predetermined site is formed by weakening an area of the catheter.

38. The method of claim 34 further comprising twisting the catheter to separate the catheter from the balloon at the predetermined site.

39. The method of claim 34 further comprising transmitting light from a light source into the balloon through at least one second lumen of the catheter.

40. The method of claim 39 wherein light is transmitted into the balloon through a different lumen of the catheter than the at least one lumen of the catheter through which the bone reinforcing mixture is introduced.

* * * * *